United States Patent
Reynolds

(10) Patent No.: US 12,285,019 B2
(45) Date of Patent: Apr. 29, 2025

(54) INSECTICIDAL PROTEINS

(71) Applicant: Syngenta Crop Protection AG, Basel (CH)

(72) Inventor: Clarence Michael Reynolds, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 316 days.

(21) Appl. No.: 17/413,743

(22) PCT Filed: Dec. 6, 2019

(86) PCT No.: PCT/US2019/064826
§ 371 (c)(1),
(2) Date: Jun. 14, 2021

(87) PCT Pub. No.: WO2020/131413
PCT Pub. Date: Jun. 25, 2020

(65) Prior Publication Data
US 2022/0061334 A1    Mar. 3, 2022

Related U.S. Application Data

(60) Provisional application No. 62/780,808, filed on Dec. 17, 2018.

(51) Int. Cl.
| | | |
|---|---|---|
| A01N 63/50 | (2020.01) | |
| A01N 63/28 | (2020.01) | |
| A01P 7/04 | (2006.01) | |
| C07K 14/36 | (2006.01) | |
| C12N 15/82 | (2006.01) | |

(52) U.S. Cl.
CPC ............ *A01N 63/50* (2020.01); *A01N 63/28* (2020.01); *A01P 7/04* (2021.08); *C07K 14/36* (2013.01); *C12N 15/8286* (2013.01)

(58) Field of Classification Search
None
See application file for complete search history.

(56) References Cited

U.S. PATENT DOCUMENTS

| 6,682,925 B1 | 1/2004 | Lehman |
| 2006/0191034 A1 | 8/2006 | Baum |

FOREIGN PATENT DOCUMENTS

| EP | 0690916 | 3/2005 |
| WO | 2018/084936 A1 | 5/2018 |

OTHER PUBLICATIONS

UniProtKB Accession No. Q12306 (version 164 published Nov. 22, 2017) (Year: 2017).*
Amino Acid Sequence published as UniProtKB Accession No. A0A1R3TSS3_9HYPH (version 4 dated Oct. 25, 2017), 1 total page. (Year: 2017).*
International Search Report mailed in International Application No. PCT/US19/64826 filed Dec. 6, 2019, mailed Apr. 14, 2020.
Extended ESR for EP19900770.9, mailed on Aug, 10, 2022, (6 total pages).
GenBank: TDC22832.1, May 13, 2019, (2 total pages).
NCBI Reference Sequence: WP_107471967.1, Apr. 11, 2018, (1 total page).

* cited by examiner

*Primary Examiner* — Matthew R Keogh
*Assistant Examiner* — Rebecca Stephens
(74) *Attorney, Agent, or Firm* — Syngenta Participations AG

(57) ABSTRACT

Compositions and methods for controlling insect pests are disclosed. In particular, novel insecticidal proteins having toxicity to at least coleopteran insect pests are provided. Nucleic acid molecules encoding the novel insecticidal proteins are also provided. Methods of making the insecticidal proteins and methods of using the insecticidal proteins and nucleic acids encoding the insecticidal proteins of the invention, for example in transgenic plants to confer protection from insect damage, are also disclosed.

12 Claims, No Drawings
Specification includes a Sequence Listing.

INSECTICIDAL PROTEINS

RELATED APPLICATION INFORMATION

This application is a 371 of International Application No. PCT/US2019/064826, filed Dec. 6, 2019, which claims priority to U.S. Provisional Application No. 62/780,808, filed Dec. 17, 2018, the contents of each of which are incorporated herein by reference herein.

STATEMENT REGARDING ELECTRONIC SUBMISSION OF A SEQUENCE LISTING

A Sequence Listing in ASCII text format, submitted under 37 C.F.R. § 1.821, entitled "81720-US_ST25.txt", 35,020 bytes in size, generated on Jun. 9, 2021 and filed via EFS-Web is provided in lieu of a paper copy. This Sequence Listing is hereby incorporated by reference into the specification for its disclosures.

FIELD OF THE INVENTION

The present invention relates to the fields of protein engineering, plant molecular biology and pest control. More particularly the invention relates to a novel protein and its variants having insecticidal activity, nucleic acids whose expression results in the insecticidal proteins, and methods of making and methods of using the insecticidal proteins and corresponding nucleic acids to control insects.

BACKGROUND

Insect pests are a major cause of crop losses. In the United States alone, billions of dollars are lost every year due to infestation by various genera of insects. In addition to losses in field crops, insect pests are also a burden to vegetable and fruit growers, to producers of ornamental flowers, and they are a nuisance to gardeners and homeowners.

Species of corn rootworm are considered to be the most destructive corn pests. In the United States alone, three species, *Diabrotica virgifera virgifera*, the western corn rootworm, *D. longicornis barberi*, the northern corn rootworm and *D. undecimpunctata howardi*, the southern corn rootworm, cause over one billion dollars in damage to corn each year in the US corn belt. An important corn rootworm pest in the Southern US is the Mexican corn rootworm, *Diabrotica virgifera zeae*. In South America, *Diabrotica speciosa* is considered to be an important pest of corn. Western corn rootworm spread to Europe in 1992 and since 2008 has been causing economic damage throughout the major corn growing regions. Corn rootworm larvae cause the most substantial plant damage by feeding almost exclusively on corn roots. This injury has been shown to increase plant lodging, to reduce grain yield and vegetative yield as well as alter the nutrient content of the grain. Larval feeding also causes indirect effects on corn by opening avenues through the roots for bacterial and fungal infections which lead to root and stalk rot diseases. Adult corn rootworms are active in cornfields in late summer where they feed on ears, silks and pollen, thus interfering with normal pollination.

Corn rootworms are mainly controlled by intensive applications of chemical pesticides, which are active through inhibition of insect growth, prevention of insect feeding or reproduction, or cause death. Good corn rootworm control can thus be reached, but these chemicals can sometimes also affect other, beneficial organisms. Another problem resulting from the wide use of chemical pesticides is the appearance of resistant insect populations. Yet another problem is due to the fact that corn rootworm larvae feed underground thus making it difficult to apply rescue treatments of insecticides. Therefore, most insecticide applications are made prophylactically at the time of planting. This practice results in a large environmental burden. This has been partially alleviated by various farm management practices, but there is an increasing need for alternative pest control mechanisms.

Biological pest control agents, such as *Bacillus thuringiensis* (Bt) strains expressing pesticidal toxins like δ-endotoxins (delta-endotoxins; also called crystal toxins or Cry proteins), have been applied to crop plants on a small scale with satisfactory results against certain insect pests. The δ-endotoxins are proteins held within a crystalline matrix that are known to possess insecticidal activity when ingested by certain insects. Such Cry proteins from *Bacillus thuringiensis* have been expressed in transgenic crop plants and exploited commercially to control certain lepidopteran and coleopteran insect pests. For example, starting in 2003, transgenic corn hybrids that control corn rootworm by expressing a Cry3Bb1, Cry34Ab1/Cry35Ab1, modified Cry3A (mCry3A) or eCry3.1 Ab protein have been available commercially in the US.

Although the use of transgenic plants expressing Cry proteins has been shown to be extremely effective, insect pests that now have resistance against the Cry proteins expressed in certain transgenic plants are known. Therefore, there remains a need to identify new and effective pest control proteins that provide an economic benefit to farmers and that are environmentally acceptable. Particularly needed are proteins that are toxic to *Diabrotica* species, a major pest of corn, that have a different mode of action than the Cry proteins in existing insect control products as a way to mitigate the development of resistance. Furthermore, delivery of insect control proteins through products that minimize the burden on the environment, as through transgenic plants, are desirable.

SUMMARY

In view of these needs, the present invention provides insecticidal proteins derived particularly from bacteria in the genus *Streptomyces*, but may be derived from other types of bacteria as well. Examples of such insecticidal proteins are exemplified herein and this class of insecticidal proteins, whether derived from *Streptomyces* or other different bacteria is collectively designated *Streptomyces* Insecticidal Proteins (SMIPs). The invention also provides variants of the SMIPs of the invention, and proteins which are substantially identical to the SMIPs of the invention and their variants. Examples of amino acid sequences of SMIPs of the invention, include, but are not limited to any of SEQ ID NOs:1-17. The SMIPs of the invention have toxicity to insect pests. For example, the SMIPs of the invention can be used to control economically important insect pests, including coleopteran insects such as western corn rootworm (WCR; *Diabrotica virgifera virgifera*), northern corn rootworm (NCR; *D. longicornis barberi*), southern corn rootworm (SCR; *D. undecimpunctata howardi*) and/or Mexican corn rootworm (MCR; *D. virgifera zeae*).

The invention further provides nucleic acid molecules comprising one or more nucleotide sequences that encode a SMIP and/or a variant of a SMIP, their complements, or nucleotide sequences that are substantially identical to a SMIP and/or a variant SMIP. Examples of nucleotide sequences that encode a SMIP or variant SMIP of the invention include, but are not limited to, any of SEQ ID NOs:18-40.

Also provided by the invention are vectors comprising recombinant nucleic acids that encode a SMIP or variant SMIP of the invention; a plant or microorganism which includes and enables expression of such nucleic acids; plants transformed with such nucleic acids, for example transgenic corn (*Zea mays* or maize) plants; the progeny of such plants which contain the nucleic acids stably incorporated and hereditable in a Mendelian manner, and/or the seeds of such plants and such progeny. The invention also provides methods of breeding to introduce a transgene comprising a nucleic acid molecule of the invention into a progeny plant and into various germplasms.

The invention also provides compositions and formulations containing a SMIP or a variant SMIP of the invention, which are capable of inhibiting the ability of insect pests to survive, grow and/or reproduce, or of limiting insect-related damage or loss to crop plants, for example applying a SMIP, or variant thereof, as part of compositions or formulations to insect-infested areas or plants, or to prophylactically treat insect-susceptible areas or plants to confer protection against the insect pests.

The invention further provides a method of making a SMIP, or variant thereof, and to methods of using the nucleic acids, for example in microorganisms to control insects or in transgenic plants to confer protection from insect damage.

The SMIPs and/or variant SMIPs of the invention can be used singly or in combination with other insect control agents and strategies to confer enhanced pest control efficiency against the same insect pest and/or to increase the spectrum of target insects with minimal environmental impact.

Other aspects and advantages of the invention will become apparent to those skilled in the art from a study of the following description of the invention and non-limiting examples.

BRIEF DESCRIPTION OF THE SEQUENCES IN THE SEQUENCE LISTING

SEQ ID NO:1 is a *Streptomyces* StrepF5053CRW (SMIP1Aa) amino acid sequence.
SEQ ID NO:2 is a SMIP1Aa-A71L amino acid sequence.
SEQ ID NO:3 is a SMIP1Aa-A90L amino acid sequence.
SEQ ID NO:4 is a SMIP1Aa-C92L amino acid sequence.
SEQ ID NO:5 is a SMIP1Aa-C92S amino acid sequence.
SEQ ID NO:6 is a SMIP1Aa-G84L amino acid sequence.
SEQ ID NO:7 is a SMIP1Aa-G85L amino acid sequence.
SEQ ID NO:8 is a SMIP1Aa-V76L amino acid sequence.
SEQ ID NO:9 is a SMIP1Aa-W78F amino acid sequence.
SEQ ID NO:10 is a SMIP1Aa-A71L/A90L amino acid sequence.
SEQ ID NO:11 is a SMIP1Aa-A71L/W78F amino acid sequence.
SEQ ID NO:12 is a SMIP1Aa-W78F/C92L amino acid sequence.
SEQ ID NO:13 is a SMIP1Aa-Y82F/I83L amino acid sequence.
SEQ ID NO:14 is a SMIP1Aa-A2G/A3G amino acid sequence.
SEQ ID NO:15 is a SMIP1Aa-A2V/A3V amino acid sequence.
SEQ ID NO:16 is a SUMO-SMIP1Aa amino acid sequence.
SEQ IS NO:17 is a *Streptomyces* Strep8K308CRW (SMIP2Aa) amino acid sequence.
SEQ ID NO:18 is a StrepF5053CRW (SMIP1Aa) nucleotide sequence.
SEQ ID NO:19 is a Strep8K308CRW (SMIP2Aa) nucleotide sequence.
SEQ ID NO:20 is a SMIP1Aa *E. coli* optimized nucleotide sequence.
SEQ ID NO:21 is a SMIP1Aa-A71L *E. coli* optimized nucleotide sequence.
SEQ ID NO:22 is a SMIP1Aa-A90L *E. coli* optimized nucleotide sequence.
SEQ ID NO:23 is a SMIP1Aa-C92L *E. coli* optimized nucleotide sequence.
SEQ ID NO:24 is a SMIP1Aa-C92S *E. coli* optimized nucleotide sequence.
SEQ ID NO:25 is a SMIP1Aa-G84L *E. coli* optimized nucleotide sequence.
SEQ ID NO:26 is a SMIP1Aa-G85L *E. coli* optimized nucleotide sequence.
SEQ ID NO:27 is a SMIP1Aa-V76L *E. coli* optimized nucleotide sequence.
SEQ ID NO:28 is a SMIP1Aa-W78F *E. coli* optimized nucleotide sequence.
SEQ ID NO:29 is a SMIP1Aa-A71L/A90L *E. coli* optimized nucleotide sequence.
SEQ ID NO:30 is a SMIP1Aa-A71L/W78F *E. coli* optimized nucleotide sequence.
SEQ ID NO:31 is a SMIP1Aa-W78F/C92L *E. coli* optimized nucleotide sequence.
SEQ ID NO:32 is a SMIP1Aa-Y82F/I83L *E. coli* optimized nucleotide sequence.
SEQ ID NO:33 is a SMIP1Aa-A2G/A3G *E. coli* optimized nucleotide sequence.
SEQ ID NO:34 is a SMIP1Aa-A2V/A3V *E. coli* optimized nucleotide sequence.
SEQ ID NO:35 is a SUMO-SMIP1Aa *E. coli* optimized nucleotide sequence.
SEQ ID NO:36 is a SMIP2Aa *E. coli* optimized nucleotide sequence
SEQ ID NO:37 is a SMIP1Aa maize-optimized nucleotide sequence.
SEQ ID NO:38 is a SMIP1Aa-A71L/A90L maize-optimized nucleotide sequence.
SEQ ID NO:39 is a SMIP1Aa-W78F/C92L maize-optimized nucleotide sequence.
SEQ ID NO:40 is a SMIP2Aa maize-optimized nucleotide sequence

DETAILED DESCRIPTION

This description is not intended to be a detailed catalog of all the different ways in which the invention may be implemented, or all the features that may be added to the invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Nucleotide sequences provided herein are presented in the 5' to 3' direction, from left to right and are presented using the standard code for representing nucleotide bases as set forth in 37 C.F.R. §§ 1.821-1.825 and the World Intellectual Property Organization (WIPO) Standard ST.25, for example: adenine (A), cytosine (C), thymine (T), and guanine (G).

Amino acids are likewise indicated using the WIPO Standard ST.25, for example: alanine (Ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

Definitions

As utilized in accordance with the present disclosure, the following terms, unless otherwise indicated, are to be understood to have the following meanings:

As used herein and in the appended claims, the singular forms "a," "an," and "the" include plural reference unless the context clearly dictates otherwise. Thus, for example, reference to "a plant" is a reference to one or more plants and includes equivalents thereof known to those skilled in the art, and so forth.

As used herein, the word "and/or" refers to and encompasses any and all possible combinations of one or more of the associated listed items, as well as the lack of combinations when interpreted in the alternative, "or."

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). With regard to a temperature the term "about" means+1° C., preferably +0.5° C. Where the term "about" is used in the context of this invention (e.g., in combinations with temperature or molecular weight values) the exact value (i.e., without "about") is preferred.

As used herein, phrases such as "between about X and Y", "between about X and about Y", "from X to Y" and "from about X to about Y" (and similar phrases) should be interpreted to include X and Y, unless the context indicates otherwise.

As used herein, the term "amplified" means the construction of multiple copies of a nucleic acid molecule or multiple copies complementary to the nucleic acid molecule using at least one of the nucleic acid molecules as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., Diagnostic Molecular Microbiology: Principles and Applications, PERSING et al., Ed., American Society for Microbiology, Washington, D.C. (1993). The product of amplification is termed an "amplicon."

"Activity" of the insecticidal proteins of the invention is meant that the insecticidal proteins function as orally active insect control agents, have a toxic effect, and/or are able to disrupt or deter insect feeding, which may or may not cause death of the insect. When an insecticidal protein of the invention is delivered to the insect, the result is typically death of the insect, or the insect does not feed upon the source that makes the insecticidal protein available to the insect.

"Pesticidal" is defined as a toxic biological activity capable of controlling a pest, such as an insect, nematode, fungus, bacteria, or virus, preferably by killing or destroying them. "Insecticidal" is defined as a toxic biological activity capable of controlling insects, preferably by killing them. A "pesticidal agent" is an agent that has pesticidal activity. An "insecticidal agent" is an agent that has insecticidal activity.

The term "chimeric construct" or "chimeric gene" or "chimeric polynucleotide" or "chimeric nucleic acid" (or similar terms) as used herein refers to a construct or molecule comprising two or more polynucleotides of different origin assembled into a single nucleic acid molecule. The term "chimeric construct", "chimeric gene", "chimeric polynucleotide" or "chimeric nucleic acid" refers to any construct or molecule that contains, without limitation, (1) polynucleotides (e.g., DNA), including regulatory and coding polynucleotides that are not found together in nature (i.e., at least one of the polynucleotides in the construct is heterologous with respect to at least one of its other polynucleotides), or (2) polynucleotides encoding parts of proteins not naturally adjoined, or (3) parts of promoters that are not naturally adjoined. Further, a chimeric construct, chimeric gene, chimeric polynucleotide or chimeric nucleic acid may comprise regulatory polynucleotides and coding polynucleotides that are derived from different sources, or comprise regulatory polynucleotides and coding polynucleotides derived from the same source, but arranged in a manner different from that found in nature. In some embodiments of the invention, the chimeric construct, chimeric gene, chimeric polynucleotide or chimeric nucleic acid comprises an expression cassette comprising a polynucleotide of the invention under the control of regulatory polynucleotides, particularly under the control of regulatory polynucleotides functional in plants or bacteria.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

To "control" insects means to inhibit, through a toxic effect, the ability of insect pests to survive, grow, feed, and/or reproduce, or to limit insect-related damage or loss in crop plants. To "control" insects may or may not mean killing the insects, although it preferably means killing the insects.

As used herein, a "codon optimized" sequence means a nucleotide sequence wherein the codons are chosen to reflect the particular codon bias that a host cell or organism may have. This is typically done in such a way so as to preserve the amino acid sequence of the polypeptide encoded by the nucleotide sequence to be optimized. In certain embodiments, the DNA sequence of the recombinant DNA construct includes sequence that has been codon optimized for the cell (e.g., an animal, plant, or fungal cell) in which the construct is to be expressed. For example, a construct to be expressed in a plant cell can have all or parts of its sequence (e.g., the first gene suppression element or the gene expression element) codon optimized for expression in a plant. See, for example, U.S. Pat. No. 6,121,014, incorporated herein by reference.

The terms "comprises" or "comprising," when used in this specification, specify the presence of stated features, integers, steps, operations, elements, or components, but do not preclude the presence or addition of one or more other features, integers, steps, operations, elements, components, or groups thereof.

As used herein, the transitional phrase "consisting essentially of" (and grammatical variants) means that the scope of a claim is to be interpreted to encompass the specified materials or steps recited in the claim" and those that do not materially alter the basic and novel characteristic(s)" of the claimed invention. Thus, the term "consisting essentially of" when used in a claim of this invention is not intended to be interpreted to be equivalent to "comprising."

In the context of the invention, "corresponding to" or "corresponds to" means that when the amino acid sequences of variant or homolog proteins are aligned with each other, the amino acids that "correspond to" certain enumerated positions in the variant or homolog protein are those that align with these positions in a reference protein but that are not necessarily in these exact numerical positions relative to the particular reference amino acid sequence of the invention. For example, if SEQ ID NO:1 is the reference sequence and is aligned with SEQ ID NO:17, amino acid Arg (R) at position 52 (R52) of SEQ ID NO:17 "corresponds to" a Arg (R) at position 20 (R20) of SEQ ID NO:1, or for example, Tyr (Y) at position 96 (Y96) of SEQ ID NO:17 "corresponds to" His (H) at position 64 (H64) of SEQ ID NO:1.

To "deliver" a composition or a toxic protein means that the composition or toxic protein comes in contact with an insect, which facilitates the oral ingestion of the composition or toxic protein, resulting in a toxic effect and control of the insect. The composition or toxic protein can be delivered in many recognized ways, including but not limited to, transgenic plant expression, formulated protein composition(s), sprayable protein composition(s), a bait matrix, or any other art-recognized protein delivery system.

The term "domain" refers to a set of amino acids conserved at specific positions along an alignment of sequences of evolutionarily related proteins. While amino acids at other positions can vary between homologs, amino acids that are highly conserved at specific positions indicate amino acids that are likely essential in the structure, stability or function of a protein. Identified by their high degree of conservation in aligned sequences of a family of protein homologs, they can be used as identifiers to determine if any polypeptide in question belongs to a previously identified polypeptide group.

"Effective insect-controlling amount" means that concentration of an insecticidal protein that inhibits, through a toxic effect, the ability of insects to survive, grow, feed and/or reproduce, or to limit insect-related damage or loss in crop plants. "Effective insect-controlling amount" may or may not mean killing the insects, although it preferably means killing the insects.

"Expression cassette" as used herein means a nucleic acid sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The expression cassette comprising the nucleotide sequence of interest may have at least one of its components heterologous with respect to at least one of its other components. The expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter that initiates transcription only when the host cell is exposed to some particular external stimulus. In the case of a multicellular organism, such as a plant, the promoter can also be specific to a particular tissue, or organ, or stage of development.

An expression cassette comprising a nucleotide sequence of interest may be chimeric, meaning that at least one of its components is heterologous with respect to at least one of its other components. An expression cassette may also be one that comprises a native promoter driving its native gene, however it has been obtained in a recombinant form useful for heterologous expression. Such usage of an expression cassette makes it so it is not naturally occurring in the cell into which it has been introduced.

An expression cassette also can optionally include a transcriptional and/or translational termination region (i.e., termination region) that is functional in plants. A variety of transcriptional terminators are available for use in expression cassettes and are responsible for the termination of transcription beyond the heterologous nucleotide sequence of interest and correct mRNA polyadenylation. The termination region may be native to the transcriptional initiation region, may be native to the operably linked nucleotide sequence of interest, may be native to the plant host, or may be derived from another source (i.e., foreign or heterologous to the promoter, the nucleotide sequence of interest, the plant host, or any combination thereof). Appropriate transcriptional terminators include, but are not limited to, the CAMV 35S terminator, the tml terminator, the nopaline synthase terminator and/or the pea rbcs E9 terminator. These can be used in both monocotyledons and dicotyledons. In addition, a coding sequence's native transcription terminator can be used. Any available terminator known to function in plants can be used in the context of this invention.

The term "expression" when used with reference to a polynucleotide, such as a gene, ORF or portion thereof, or a transgene in plants, refers to the process of converting genetic information encoded in a gene into RNA (e.g., mRNA, rRNA, tRNA, or snRNA) through "transcription" of the gene (i.e., via the enzymatic action of an RNA polymerase), and into protein where applicable (e.g. if a gene encodes a protein), through "translation" of mRNA. Gene expression can be regulated at many stages in the process. For example, in the case of antisense or dsRNA constructs, respectively, expression may refer to the transcription of the antisense RNA only or the dsRNA only. In embodiments, "expression" refers to the transcription and stable accumulation of sense (mRNA) or functional RNA. "Expression" may also refer to the production of protein.

A "gene" is a defined region that is located within a genome and comprises a coding nucleic acid sequence and typically also comprises other, primarily regulatory, nucleic acids responsible for the control of the expression, that is to say the transcription and translation, of the coding portion. A gene may also comprise other 5' and 3' untranslated sequences and termination sequences. Further elements that may be present are, for example, introns. The regulatory nucleic acid sequence of the gene may not normally be operatively linked to the associated nucleic acid sequence as found in nature and thus would be a chimeric gene.

"Gene of interest" refers to any nucleic acid molecule which, when transferred to an organism, such as a bacteria or a plant, confers upon the bacteria or plant a desired trait such as antibiotic resistance, virus resistance, insect resistance, disease resistance, or resistance to other pests, herbicide tolerance, abiotic stress tolerance, male sterility, modified fatty acid metabolism, modified carbohydrate metabolism, improved nutritional value, improved performance in an industrial process or altered reproductive capability. The "gene of interest" may also be one that is transferred to bacteria or plants for the production of commercially valuable enzymes or metabolites in the plant.

A "heterologous" nucleic acid sequence or nucleic acid molecule is a nucleic acid sequence or nucleic acid molecule not naturally associated with a host cell into which it is introduced, including non-naturally occurring multiple copies of a naturally occurring nucleic acid sequence. A heterologous nucleic acid sequence or nucleic acid molecule may comprise a chimeric sequence such as a chimeric expression cassette, where the promoter and the coding region are derived from multiple source organisms. The promoter sequence may be a constitutive promoter sequence, a tissue-specific promoter sequence, a chemically-inducible promoter sequence, a wound-inducible promoter sequence, a stress-inducible promoter sequence, or a developmental stage-specific promoter sequence.

A "homologous" nucleic acid sequence is a nucleic acid sequence naturally associated with a host cell into which it is introduced.

"Homologous recombination" is the reciprocal exchange of nucleic acid fragments between homologous nucleic acid molecules.

A "hypothetical protein" as used herein refers to a protein whose existence has been predicted, but for which there is a lack of experimental evidence that it is expressed in vivo. Sequencing genomes or organisms such as bacteria or plants, often results in numerous predicted open reading frames to which functions cannot be readily assigned. These proteins, either orphan or conserved hypothetical proteins, make up about 20% to about 40% of proteins encoded in each newly sequenced genome. Even when there is enough evidence that the product of a gene is expressed, by techniques such as microarray and mass-spectrometry, it is difficult to assign a function to it given its lack of identity to protein sequences with annotated biochemical function. Typically, most protein sequences are inferred from computational analysis of genomic DNA sequence. Hypothetical proteins are typically created by gene prediction software during genome analysis. When bioinformatics tools used for the gene identification find large open reading frames without a characterized homolog in a protein database, such tools typically return the designation "hypothetical protein" as an annotation remark.

The term "motif" or "consensus sequence" or "signature" refers to a short conserved region in the sequence of evolutionarily related proteins. Motifs are frequently highly conserved parts of domains, but may also include only part of the domain, or be located outside of conserved domain (if all of the amino acids of the motif fall outside of a defined domain).

The term "identity" or "identical" or "substantially identical," in the context of two nucleic acid or amino acid sequences, refers to two or more sequences or subsequences that have at least 60%, preferably at least 80%, more preferably 90%, even more preferably 95%, and most preferably at least 99% nucleotide or amino acid residue identity, when compared and aligned for maximum correspondence, as measured using one of the following sequence comparison algorithms or by visual inspection. Preferably, the substantial identity exists over a region of the sequences that is at least about 50 residues or bases in length, more preferably over a region of at least about 100 residues or bases, and most preferably the sequences are substantially identical over at least about 150 residues or bases. In an especially preferred embodiment, the sequences are substantially identical over the entire length of the coding regions. Furthermore, substantially identical nucleic acid or amino acid sequences perform substantially the same function.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2: 482 (1981), by the homology alignment algorithm of Needleman & Wunsch, J. Mol. Biol. 48: 443 (1970), by the search for similarity method of Pearson & Lipman, Proc. Nat'l. Acad Sci. USA 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity and sequence similarity is the BLAST algorithm, which is described in Altschul et al., J. Mol. Biol. 215: 403-410 (1990). Software for performing BLAST analyses is publicly available through the National Center for Biotechnology Information (National Center for Biotechnology Information, U.S. National Library of Medicine, 8600 Rockville Pike, Bethesda, MD 20894 USA). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad Sci. USA 89: 10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) Laboratory Techniques in Biochemistry and Molecular Biology-Hybridization with Nucleic Acid Probes part I chapter 2 "Overview of principles of hybridization and the strategy of nucleic acid probe assays" Elsevier, New York. Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but not to other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42°C, with the hybridization being carried out overnight. An example of highly stringent wash conditions is 0.15M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45°C for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° ° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are examples of sets of hybridization/wash conditions that may be used to clone homologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° ° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° ° C. with washing in 0.1×SSC, 0.1% SDS at 65° C.

A further indication that two nucleic acid sequences or proteins are substantially identical is that the protein encoded by the first nucleic acid is immunologically cross reactive with, or specifically binds to, the protein encoded by the second nucleic acid. Thus, a protein is typically substantially identical to a second protein, for example, where the two proteins differ only by conservative substitutions.

The term "isolated" nucleic acid molecule, polynucleotide or protein is a nucleic acid molecule, polynucleotide or protein that no longer exists in its natural environment. An isolated nucleic acid molecule, polynucleotide or protein of the invention may exist in a purified form or may exist in a recombinant host such as in a transgenic bacteria or a transgenic plant. Therefore, a claim to an "isolated" nucleic acid molecule, as enumerated herein, encompasses a nucleic acid molecule when the nucleic acid molecule is comprised within a transgenic plant genome.

A "nucleic acid molecule" or "nucleic acid sequence" is a segment of single- or double-stranded DNA or RNA that can be isolated from any source. In the context of the invention, the nucleic acid molecule is typically a segment of DNA. In some embodiments, the nucleic acid molecules of the invention are isolated nucleic acid molecules.

"Operably linked" refers to the association of polynucleotides on a single nucleic acid fragment so that the function of one affects the function of the other. For example, a promoter is operably linked with a coding polynucleotide or functional RNA when it is capable of affecting the expression of that coding polynucleotide or functional RNA (i.e., that the coding polynucleotide or functional RNA is under the transcriptional control of the promoter). Coding polynucleotide in sense or antisense orientation can be operably linked to regulatory polynucleotides.

As used herein "pesticidal," insecticidal," and the like, refer to the ability of a SMIP toxin of the invention to control a pest organism or an amount of a SMIP toxin that can control a pest organism as defined herein. Thus, a pesticidal SMIP toxin can kill or inhibit the ability of a pest organism (e.g., insect pest) to survive, grow, feed, or reproduce.

The terms "protein," "peptide" and "polypeptide" may be used interchangeably herein.

A "plant" is any plant at any stage of development, particularly a seed plant. Exemplary plants include, but are not limited to, corn (*Zea mays*), canola (*Brassica napus, Brassica rapa* ssp.), alfalfa (*Medicago saliva*), rice (*Oryza sativa*, including without limitation Indica and/or *Japonica* varieties), rape (*Brassica napus*), rye (*Secale cereale*), sorghum (*Sorghum bicolor, Sorghum vulgare*), sunflower (*Helianthus annus*), wheat (*Triticum aestivum*), soybean (*Glycine max*), tobacco (*Nicotiana tobacum*), potato (*Solanum tuberosum*), peanut (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus* amygdalus), sugar beets (*Beta vulgaris*), apple (*Malus pumila*), blackberry (*Rubus*), strawberry (*Fragaria*), walnut (*Juglans regia*), grape (*Vitis vinifera*), apricot (*Prunus armeniaca*), cherry (*Prunus*), peach (*Prunus persica*), plum (*Prunus domestica*), pear (*Pyrus communis*), watermelon (*Citrullus vulgaris*), duckweed (*Lemna* spp.), oats (*Avena sativa*), barley (*Hordium vulgare*), vegetables, ornamentals, conifers, and turfgrasses (e.g., for ornamental, recreational or forage purposes), and biomass grasses (e.g., switchgrass and *miscanthus*).

Vegetables include without limitation Solanaceous species (e.g., tomatoes; *Lycopersicon esculentum*), lettuce (e.g., *Lactuca sativa*), carrots (*Caucus carota*), cauliflower (*Brassica oleracea*), celery (*Apium graveolens*), eggplant (*Solanum melongena*), asparagus (*Asparagus officinalis*), ochra (*Abelmoschus esculentus*), green beans (*Phaseolus vulgaris*), lima beans (*Phaseolus limensis*), peas (*Lathyrus* spp.), members of the genus *Cucurbita* such as hubbard squash (*C. hubbard*), butternut squash (*C. moschata*), zucchini (*C. pepo*), crookneck squash (*C. crookneck*), *C. argyrosperma, C. argyrosperma* ssp *sororia, C. digitata, C. ecuadorensis, C. foetidissima, C. lundelliana*, and *C. martinezii*, and members of the genus *Cucumis* such as cucumber (*Cucumis sativus*), cantaloupe (*C. cantalupensis*), and musk melon (*C. melo*).

Ornamentals include without limitation azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus* caryophyllus), poinsettia (*Euphorbia pulcherima*), and chrysanthemum.

Conifers, which may be employed in practicing the present invention, include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

Turfgrass include but are not limited to zoysiagrasses, bentgrasses, fescue grasses, bluegrasses, St. Augustinegrasses, bermudagrasses, buffalograsses, ryegrasses, and orchardgrasses.

Also included are plants that serve primarily as laboratory models, e.g., *Arabidopsis*.

A "plant cell" is a structural and physiological unit of a plant, comprising a protoplast and a cell wall. The plant cell may be in the form of an isolated single cell or a cultured cell, or as a part of a higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

A "polynucleotide" refers to a polymer composed of many nucleotide monomers covalently bonded in a chain. Such "polynucleotides" includes DNA, RNA, modified oligo nucleotides (e.g., oligonucleotides comprising bases that are not typical to biological RNA or DNA, such as 2'-O-methylated oligonucleotides), and the like. In some embodiments, a nucleic acid or polynucleotide can be single-stranded, double-stranded, multi-stranded, or combinations thereof. Unless otherwise indicated, a particular nucleic acid or polynucleotide of the present invention optionally comprises or encodes complementary polynucleotides, in addition to any polynucleotide explicitly indicated.

"Polynucleotide of interest" refers to any polynucleotide which, when transferred to an organism, e.g., a plant, confers upon the organism a desired characteristic such as insect resistance, disease resistance, herbicide tolerance, antibiotic resistance, improved nutritional value, improved performance in an industrial process, production of commercially valuable enzymes or metabolites or altered reproductive capability.

A "promoter" is an untranslated DNA sequence upstream of the coding region that contains the binding site for RNA polymerase and initiates transcription of the DNA. The promoter region may also include other elements that act as regulators of gene expression.

As used herein, the term "recombinant" refers to a form of nucleic acid (e.g., DNA or RNA) or protein or an organism that would not normally be found in nature and as such was created by human intervention. As used herein, a "recombinant nucleic acid molecule" is a nucleic acid molecule comprising a combination of polynucleotides that would not naturally occur together and is the result of human intervention, e.g., a nucleic acid molecule that is comprised of a combination of at least two polynucleotides heterologous to each other, or a nucleic acid molecule that is artificially synthesized, for example, a polynucleotide synthesize using an assembled nucleotide sequence, and comprises a polynucleotide that deviates from the polynucleotide that would normally exist in nature, or a nucleic acid molecule that comprises a transgene artificially incorporated into a host cell's genomic DNA and the associated flanking DNA of the host cell's genome. Another example of a recombinant nucleic acid molecule is a DNA molecule resulting from the insertion of a transgene into a plant's genomic DNA, which may ultimately result in the expression of a recombinant RNA or protein molecule in that organism. As used herein, a "recombinant plant" is a plant that would not normally exist in nature, is the result of human intervention, and contains a transgene or heterologous nucleic acid molecule incorporated into its genome. As a result of such genomic alteration, the recombinant plant is distinctly different from the related wild-type plant.

"Regulatory elements" refer to sequences involved in controlling the expression of a nucleotide sequence. Regulatory elements comprise a promoter operably linked to the nucleotide sequence of interest and termination signals. They also typically encompass sequences required for proper translation of the nucleotide sequence.

*Streptomyces* Insecticidal Proteins (SMIPs) are proteins encoded by genes found at least in the genomes of bacteria in the family Actinmycetaceae, particularly in the Genus *Streptomyces*, that comprise aegerolysin-like pore forming domains and are active against at least insect pests in the Genus *Diabrotica*. A "variant SMIP" is a SMIP that has been engineered by making a substitution and/or deletion of at least one amino acid that is found in a naturally occurring SMIP and/or an insertion of an amino acid into a SMIP sequence. As used herein, when the term "*Streptomyces* Insecticidal Protein" or "SMIP" is used alone it is meant to include both non-engineered proteins as well as engineered variant proteins unless otherwise indicated.

The terms "substitution," "insertion" or "addition," and "deletion" are used herein with reference to amino acid or nucleotide sequences. A "substitution" refers to a replacement of one or more nucleotides or amino acids by different nucleotides or amino acids, respectively. An "insertion" or "addition" is that change in a nucleotide or amino acid sequence which has resulted in the addition of one or more nucleotides or amino acid residues, respectively, as compared to the naturally occurring sequence. A "deletion" is defined as a change in either nucleotide or amino acid sequence in which one or more nucleotides or amino acid residues, respectively, are absent. Amino acid substitutions are typically of single residues; insertions usually will be on the order of from about 1 to 20 amino acids, although considerably larger insertions may be tolerated. Deletions range from about 1 to about 20 residues, although in some cases deletions may be much larger. Substitutions, deletions, insertions, or any combination thereof may be used to arrive at a final variant polypeptide. Generally, a few amino acids are changed to minimize the alteration of the molecule. However, larger changes may be tolerated in certain circumstances. In certain embodiments, amino acid substitutions can be the result of replacing one amino acid with another amino acid having similar structural and/or chemical properties, such as the replacement of an isoleucine with a valine, i.e., conservative amino acid replacements. Insertions or deletions may optionally be in the range of 1 to 5 amino acids. In embodiments, substitutions can be made in accordance with known "conservative substitutions." A "conservative substitution" refers to the substitution of an amino acid in one class by an amino acid in the same class, where a class is defined by common physicochemical amino acid side chain properties and high substitution frequencies in homologous proteins found in nature. In contrast, in certain embodiments, substitutions are non-conservative. A "non-conservative substitution" refers to the substitution of an amino acid in one class with an amino acid from another class.

"Transformation" is a process for introducing heterologous nucleic acid into a host cell or organism. In particular embodiments, "transformation" means the stable integration of a DNA molecule into the genome (nuclear or plastid) of an organism of interest.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extra-chromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

This invention provides compositions and methods for controlling harmful insect pests. Particularly, the invention relates to insecticidal proteins, particularly *Streptomyces* Insecticidal Proteins (SMIPs), that have activity against at least coleopteran insects, for example, *Diabrotica virgifera virgifera* (western corn rootworm; WCR), *Diabrotica barberi* (northern corn rootworm; NCR), and/or *Diabrotica undecimpunctata howardi* (southern corn rootworm; SCR) and/or other *Diabrotica* species including *Diabrotica virgifera zeae* (Mexican corn rootworm). Native SMIPs are produced by gram negative bacteria in the genus *Streptomyces* and related bacteria. Examples of such SMIPs described herein include those produced by *Streptomyces* strain F5053, which produces a Strept5053CRW (SMIP1Aa) insecticidal protein and by *Streptomyces* strain 8K308, which produces a Strept8K308CRW (SMIP2Aa) insecticidal protein. In some embodiments, a novel insecticidal protein of the invention may have activity against lepidopteran insect pests, including without limitation *Agrotis ipsilon* (black cutworm), *Diatraea* saccharalis (sugar cane borer; SCB) and/or *Diatraea grandiosella* (southwestern corn borer; SWCB). The invention also relates to nucleic acids whose expression results in SMIPs of the invention, and to the making and using of the SMIPs to control insect pests. In certain embodiments, the expression of the nucleic acids results in insecticidal proteins that can be used to control at least coleopteran insects such as western corn rootworm, northern corn rootworm and/or southern corn rootworm, particularly when expressed in a transgenic plant such as a transgenic corn plant.

In some non-limiting embodiments, the invention encompasses a nucleic acid molecule, and optionally an isolated nucleic acid molecule, comprising, consisting essentially of or consisting of a nucleotide sequence that encodes a protein that is toxic to an insect pest, i.e. an insecticidal protein, wherein the nucleotide sequence (a) encodes a protein comprising an amino acid sequence that has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with any of SEQ ID NOs:1-17, or a toxin fragment thereof; or (b) has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with any of SEQ ID NOs: 18-40, or a toxin-encoding fragment thereof; or (c) is a synthetic sequence of (a) or (b) that has codons optimized for expression in a transgenic organism. In other embodiments, the insecticidal protein comprises, consists essentially of or consists of an amino acid sequence of any of SEQ ID NOs:1-17, or a toxic fragment thereof. In other embodiments, the nucleotide sequence comprises, consists essentially of or consists of any of SEQ ID NOs:18-40, or a toxin-encoding fragment thereof.

In some non-limiting embodiments, the invention encompasses a chimeric gene comprising a heterologous promoter operably linked to a nucleic acid molecule comprising, consisting essentially of or consisting of a nucleotide sequence that encodes a protein that is toxic to an insect pest, wherein the nucleotide sequence (a) encodes a protein comprising an amino acid sequence that has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with any of SEQ ID NOs: 1-17, or a toxin fragment thereof; or (b) has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with any of SEQ ID NOs: 18-40, or a toxin-encoding fragment thereof; or (c) is a synthetic sequence of (a) or (b) that has codons optimized for expression in a transgenic organism. In other embodiments, the insecticidal protein comprises an amino acid sequence of any of SEQ ID NOs:1-17, or a toxic fragment thereof. In other embodiments, the nucleotide sequence comprises any of SEQ ID NOs:18-40, or a toxin-encoding fragment thereof. In some aspects of these embodiments, the chimeric gene is an expression cassette.

In other non-limiting embodiments, the promoter comprised in a chimeric gene or an expression cassette of the invention is a plant expressible promoter. In aspects of these embodiments, the plant expressible promoter is selected from the group of promoters consisting of ubiquitin, cestrum yellow virus, corn TrpA, OsMADS 6, maize H3 histone, bacteriophage T3 gene 9 5' UTR, corn sucrose synthetase 1, corn alcohol dehydrogenase 1, corn light harvesting complex, corn heat shock protein, maize mtl, pea small subunit RuBP carboxylase, rice actin, rice cyclophilin, Ti plasmid mannopine synthase, Ti plasmid nopaline synthase, petunia chalcone isomerase, bean glycine rich protein 1, potato patatin, lectin, CaMV 35S and S-E9 small subunit RuBP carboxylase promoter.

In some non-limiting embodiments, the insecticidal protein encoded by a nucleic acid molecule of the invention or a chimeric gene of the invention or an expression cassette of the invention is active against a coleopteran insect pest. In some aspects of these embodiments, the coleopteran insect pest is in the Genus *Diabrotica*. In other aspects, the *Diabrotica* insect pest is *Diabrotica virgifera virgifera* (western corn rootworm; WCR), *Diabrotica barberi* (northern corn rootworm; NCR), and/or *Diabrotica undecimpunctata howardi* (southern corn rootworm; SCR) and/or other *Diabrotica* species including *Diabrotica virgifera zeae* (Mexican corn rootworm; MCR).

In some non-limiting embodiments, a chimeric gene or expression cassette of the invention comprises a nucleotide sequence that encodes a SMIP of the invention, wherein the nucleotide sequence is codon optimized for expression in a transgenic organism. In some embodiments, the transgenic organism is a bacteria or a plant.

In other non-limiting embodiments, the transgenic bacteria comprising a codon optimized sequence of the invention is in the genus *Bacillus, Clostridium, Xenorhabdus, Photorhabdus, Pasteuria, Escherichia, Pseudomonas, Erwinia, Serratia, Klebsiella, Salmonella, Pasteurella, Xanthomonas, Streptomyces, Rhizobium, Rhodopseudomonas, Sinorhizobium, Ensifer, Methylophilius, Agrobacterium, Acetobacter, Lactobacillus, Arthrobacter, Azotobacter, Leuconostoc, Sphingomonas, Burkholderia, Candidatus Glomeribacter, Dyella, Herbaspirillum, Bradyrhizobium, Staphylococcus, Methylophilus, Variovorax, Streptococcus, Chitinophaga* or *Alcaligenes*. In other embodiments, the transgenic bacteria is *Escherichia coli*. In other embodiments, the nucleotide sequence comprises, consists essentially of or consists of any of SEQ ID NOs:20-36.

In other non-limiting embodiments, the transgenic plant comprising a codon optimized sequence of the invention is a monocot plant or a dicot plant. In still other embodiments, the dicot plant is selected from the group consisting of a soybean, sunflower, tomato, cole crop, cotton, sugar beet and tobacco. In other embodiments, the monocot plant is selected from the group consisting of barley, maize, oat, rice, sorghum, sugarcane and wheat. In other embodiments, the transgenic plant is a maize plant. In other embodiments, the nucleotide sequence comprises codons optimized for expression in maize. In still other embodiments, the nucleotide sequence comprises, consists essentially of or consists of any of SEQ ID NOs:37-40.

In some non-limiting embodiments, the invention encompasses a protein, and optionally an isolated protein, that is toxic to an insect pest, i.e. an insecticidal protein, wherein the protein or isolated protein comprises, consists essentially of or consists of (a) an amino acid sequence that has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with any of SEQ ID NOs:1-17, or a toxin fragment thereof; or (b) an amino acid sequence that comprises, consists essentially of or consists of any of SEQ ID NOs:1-17, or a toxin fragment thereof; or (c) an amino acid sequence that is encoded by a nucleotide sequence that has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with any of SEQ ID NOs:18-40, or a toxin-encoding fragment thereof; or (d) an amino acid sequence that is encoded by a nucleotide sequence comprising, consisting essentially of or consisting of any of SEQ ID NOs:18-40, or a toxin-encoding fragment thereof. Those skilled in the art will recognize that modifications can be made to the exemplified insecticidal proteins encompassed by the invention. Such modifications and resulting substantially identical nucleic acid or amino acid molecules are encompassed by the present invention.

The invention also encompasses an engineered *Streptomyces* Insecticidal Protein (eSMIP), which can be described as a mutant SMIP or a variant SMIP or a modified SMIP of the invention. In some embodiments, the modification can comprise a substitution and/or deletion of one or more amino acids in a naturally occurring SMIP sequence and/or insertion of one or more additional amino acids into a naturally occurring SMIP sequence. In other embodiments, the modification can comprise a substitution and/or deletion and/or insertion of one or more amino acids in an engineered SMIP. The substitution and/or insertion may be with a naturally occurring amino acid or a non-naturally occurring amino acid. In some non-limiting embodiments, the modification comprises, consists essentially of or consists of an substitution and/or insertion and/or deletion of one or more of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and/or valine amino acids at an amino acid position of a SMIP amino acid sequence. Such a substitution and/or insertion and/or deletion may be accomplished by changing codons in a nucleotide sequence that encodes a SMIP resulting in the modified SMIP nucleotide sequence encoding an eSMIP, which is a mutant SMIP or a variant SMIP or a modified SMIP of the invention.

In some non-limiting embodiments, the SMIP is modified by substitution and/or insertion of (a) one or more amino acids with an aliphatic hydrophobic side chain (e.g., alanine, isoleucine, methionine and/or valine; in embodiments, the amino acid is not an alanine); or (b) one or more amino acids with an aromatic hydrophobic side chain (e.g., phenylalanine, tryptophan and/or tyrosine); or (c) one or more amino acids with a polar neutral side chain (e.g., asparagine, cysteine, glutamine, serine and/or threonine); or (d) one or more amino acids with an acidic side chain (e.g., aspartic acid and/or glutamic acid); one or more amino acids with a basic side chain (e.g., arginine, histidine and/or lysine); or (e) one or more glycine residues; or (f) one or more proline residues; or (g) any combination of (a) to (f).

In some embodiments, the invention encompasses an engineered insecticidal protein comprising, consisting essentially of or consisting of an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:1 and further comprising at least one mutation at a position that corresponds to amino acid positions 1-118 of SEQ ID NO:1.

In some embodiments, the mutation is at an amino acid positon that corresponds to amino acid position 2, 3, 71, 76, 78, 82, 83, 84, 85, 90 or 92 of SEQ ID NO: 1, or any combination thereof. In other non-limiting embodiments, the mutation is at position 2, 3, 71, 76, 78, 82, 83, 84, 85, 90 or 92 of SEQ ID NO:1. In other embodiments, the mutation is at a position corresponding to amino acids 2 and 3, or 71 and 78, or 71 and 90, or 78 and 92, or 82 and 83 of SEQ ID NO:1. In further embodiments, the mutation is at amino acid positions 2 and 3, or 71 and 78, or 71 and 90, or 78 and 92, or 82 and 83 of SEQ ID NO:1. In other embodiments, the mutation at position 2 is A2G or A2V, the mutation at position 3 is A3G or A3V, the mutation at position 71 is A71L, the mutation at position 76 is V76L, the mutation at position 78 is W78F, the mutation at position 82 is Y82F, the mutation at position 83 is I83L, the mutation at position 84 is G84L, the mutation at position 85 is G85L, the mutation at position 90 is A90L, or the mutation at position 92 is C92S or C92L. In other embodiments, the mutation at positions 2 and 3 is A2G/A3G or A2V/A3V, the mutation at position 71 and 78 is A71L/W78F, the mutation at positions 71 and 90 is A71L/A90L, the mutation at positions 78 and 92 is W78F/C92L, or the mutation at positions 82 and 83 is Y82F/I83L.

In some embodiments, the protein comprises, consists essentially of or consists of an amino acid sequence of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14 or SEQ ID NO:15.

In some embodiments, the invention encompasses an engineered insecticidal protein comprising, consisting essentially of or consisting of an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with SEQ ID NO:17 and further comprising at least one mutation at a position that corresponds to amino acid positions 33-150 of SEQ ID NO:17.

In some embodiments, the mutation is at an amino acid position 34, 35, 103, 108, 110, 114, 115, 116, 117, 122 or 124 of SEQ ID NO:17, or any combination thereof. In other embodiments, the mutation is at amino acid position 34, 35, 103, 108, 110, 114, 115, 116, 117, 122 or 124 of SEQ ID NO:17, or any combination thereof. In still other embodiments, the mutation is at a position corresponding to amino acids 34 and 35, or 103 and 110, or 103 and 122, or 110 and 124, or 114 and 115 of SEQ ID NO:17. In still further embodiments, the mutation is at amino acids 34 and 35, or 103 and 110, or 103 and 122, or 110 and 124, or 114 and 115 of SEQ ID NO:17. In other embodiments, the mutation at position 34 is A34G or A34V, the mutation at position 35 is A35G or A35V, the mutation at position 103 is A103L, the mutation at position 108 is V108L, the mutation at position 110 is W110F, the mutation at position 114 is Y114F, the mutation at position 115 is V115L, the mutation at position 116 is G116L, the mutation at position 117 is S117L, the mutation at position 122 is A122L, or the mutation at position 124 is C124S or C124L. In still other embodiments, the mutation at positions 34 and 35 is A34G/A35G or A34V/A35V, the mutation at position 103 and 110 is A103L/W110F, the mutation at positions 103 and 122 is A103L/

A122L, the mutation at positions 110 and 124 is W110F/ C124L, or the mutation at positions 114 and 115 is Y114F/ V115L.

In some non-limiting embodiments, the mutant or variant SMIPs of the invention have enhanced digestion by a mammalian digestive protease (e.g., pepsin) as compared with a suitable control and/or the parental molecule not containing a modification of the invention when tested under the same conditions (e.g., enzyme concentration, protein concentration, pH, temperature and/or time). Methods for assessing protein digestion by pepsin and other digestive proteases are known in the art, for example, the Simulated Gastric Fluid (SGF) assay described in Example 2. For example, digestion with pepsin can be carried out at approximately 37° C. and approximately pH 1.2, optionally with an enzyme concentration of approximately 10 Units (U) pepsin per microgram of protein. In other embodiments, the digestibility of a SMIP of the invention is enhanced by substitution mutation of an amino acid at a position corresponding to amino acid position 71, 78, 90 or 92 of SEQ ID NO:1, or any combination thereof, or the digestibility is enhanced by substitution mutation of an amino acid at a position corresponding to amino acid position 103, 110, 122 or 124 of SEQ ID NO: 17, or any combination thereof. In still other embodiments, the mutation is at a position corresponding to amino acids 71 and 90, or 78 and 92 of SEQ ID NO:1. In other embodiments, the mutation is at a position corresponding to amino acids 103 and 122, or 110 and 124 of SEQ ID NO:17. In still other embodiments, the amino acid that corresponds to position 71 of SEQ ID NO:1 is substituted with a Lue (L), the amino acid that corresponds to position 78 of SEQ ID NO:1 is substituted with a Phe (F), the amino acid that corresponds to position 90 of SEQ ID NO:1 is substituted with a Leu (L) or the amino acid that corresponds to position 92 of SEQ ID NO:1 is substituted with a Leu (L), or any combination thereof. In still other embodiments, the amino acid that corresponds to position 103 of SEQ ID NO:17 is substituted with a Lue (L), the amino acid that corresponds to position 110 of SEQ ID NO:17 is substituted with a Phe (F), the amino acid that corresponds to position 122 of SEQ ID NO:17 is substituted with a Leu (L) or the amino acid that corresponds to position 124 of SEQ ID NO:17 is substituted with a Leu (L), or any combination thereof.

In some embodiments, the digestibility of a SMIP of the invention is enhanced by substitution mutation of an amino acid at position 71, 78, 90 or 92 of SEQ ID NO:1, or any combination thereof. In other embodiments, the mutation is at a position 71 and 90, or 78 and 92 of SEQ ID NO:1. In still other embodiments, the mutation at position 71 of SEQ ID NO:1 is A71L, the mutation at position 78 of SEQ ID NO: 1 is W78F, the mutation at position 90 of SEQ ID NO:1 is A90L or the mutation at position 92 of SEQ ID NO:1 is C92L, or any combination thereof. In still further embodiments, the mutant or variant SMIP1Aa protein having enhanced digestibility in an SGF assay comprises, consists essentially of or consists of SEQ ID NO:2, SEQ ID NO:3, SEQ ID NO:4, SEQ ID NO:9, SEQ ID NO: 10 or SEQ ID NO:12.

In some embodiments, a SMIP toxin of the invention, including eSMIPs of the invention, are active against a coleopteran insect pest. Insects in the order Coleoptera include but are not limited to any coleopteran insect now known or later identified including those in suborders Archostemata, Myxophaga, Adephaga and Polyphaga, and any combination thereof.

In some non-limiting embodiments, the insecticidal proteins of the invention are active against a *Diabrotica* species. *Diabrotica* is a genus of beetles of the order Coleoptera commonly referred to as "corn rootworm" or "cucumber beetle." Exemplary *Diabrotica* species include without limitation *Diabrotica longicornis barberi* (northern corn rootworm), *D. virgifera virgifera* (western corn rootworm), *D. undecimpunctata howardii* (southern corn rootworm), *D. balteata* (banded cucumber beetle), *D. undecimpunctata undecimpunctata* (western spotted cucumber beetle), *D. significata* (3-spotted leaf beetle), *D. speciosa* (chrysanthemum beetle), *D. virgifera zeae* (Mexican corn rootworm), *D. beniensis, D. cristata, D. curviplustalata, D. dissimilis, D. elegantula, D. emorsitans, D. graminea, D. hispanloe, D. lemniscata, D. linsleyi, D. milleri, D. nummularis, D. occlusal, D. porrecea, D. scutellata, D. tibialis, D. trifasciata* and *D. viridula*; and any combination thereof.

Other non-limiting examples of coleopteran insect pests according to the invention include *Leptinotarsa* spp. such as *L. decemlineata* (Colorado potato beetle); *Chrysomela* spp. such as *C. scripta* (cottonwood leaf beetle); *Hypothenemus* spp. such as *H. hampei* (coffee berry borer); *Sitophilus* spp. such as *S. zeamais* (maize weevil); *Epitrix* spp. such as *E. hirtipennis* (tobacco flea beetle) and *E. cucumeris* (potato flea beetle); *Phyllotreta* spp. such as *P. cruciferae* (crucifer flea beetle) and *P. pusilla* (western black flea beetle); *Anthonomus* spp. such as *A. eugenii* (pepper weevil); *Hemicrepidus* spp. such as *H. memnonius* (wireworms); *Melanotus* spp. such as *M. communis* (wireworm); *Ceutorhychus* spp. such as *C. assimilis* (cabbage seedpod weevil); *Phyllotreta* spp. such as *P. cruciferae* (crucifer flea beetle); *Aeolus* spp. such as *A. mellillus* (wireworm); *Aeolus* spp. such as *A. mancus* (wheat wireworm); *Horistonotus* spp. such as *H. uhlerii* (sand wireworm); *Sphenophorus* spp. such as *S. maidis* (maize billbug), *S. zeae* (timothy billbug), *S. parvulus* (bluegrass billbug), and *S. callosus* (southern corn billbug); *Phyllophaga* spp. (White grubs); *Chaetocnema* spp. such as *C. pulicaria* (corn flea beetle); *Popillia* spp. such as *P. japonica* (Japanese beetle); *Epilachna* spp. such as *E. varivestis* (Mexican bean beetle); *Cerotoma* spp. such as *C. trifurcate* (Bean leaf beetle); *Epicauta* spp. such as *E. pestifera* and *E. lemniscata* (Blister beetles); and any combination of the foregoing.

The insecticidal proteins of the invention may also be active against insects in the order Lepidoptera. Such lepidopteran insects include, without limitation any insect now known or later identified that is classified as a lepidopteran insect, including those insect species within suborders Zeugloptera, Glossata, and Heterobathmiina, and any combination thereof. Exemplary lepidopteran insects include, but are not limited to, *Ostrinia* spp. such as *O. nubilalis* (European corn borer); *Plutella* spp. such as *P. xylostella* (diamondback moth); *Spodoptera* spp. such as *S. frugiperda* (fall armyworm), *S. ornithogalli* (yellowstriped armyworm), *S. praefica* (western yellowstriped armyworm), *S. eridania* (southern armyworm) and *S. exigua* (beet armyworm); *Agrotis* spp. such as *A. ipsilon* (black cutworm), *A. segetum* (common cutworm), *A. gladiaria* (claybacked cutworm), and *A. orthogonia* (pale western cutworm); *Striacosta* spp. such as *S. albicosta* (western bean cutworm); *Helicoverpa* spp. such as *H. zea* (corn earworm), *H. punctigera* (native budworm), *S. littoralis* (Egyptian cotton leafworm) and *H. armigera* (cotton bollworm); *Heliothis* spp. such as *H. virescens* (tobacco budworm); *Diatraea* spp. such as *D. grandiosella* (southwestern corn borer) and *D. saccharalis* (sugarcane borer); *Trichoplusia* spp. such as *T. ni* (cabbage looper); *Sesamia* spp. such as *S. nonagroides* (Mediterranean corn borer); *Pectinophora* spp. such as *P. gossypiella* (pink bollworm); *Cochylis* spp. such as *C. hospes* (banded sunflower moth); *Manduca* spp. such as *M. sexta* (tobacco hornworm) and *M. quinquemaculata* (tomato hornworm); *Elasmopalpus* spp. such as *E. lignosellus* (lesser cornstalk borer); *Pseudoplusia* spp. such as *P. includens* (soybean looper); *Anticarsia* spp. such as *A. gemmatalis* (velvetbean caterpillar); *Plathypena* spp. such as *P. scabra* (green cloverworm); *Pieris* spp. such as *P. brassicae* (cabbage butterfly), *Papaipema* spp. such as *P. nebris* (stalk borer); *Pseudaletia* spp. such as *P. unipuncta* (common armyworm); *Peridroma* spp. such as *P. saucia* (variegated cutworm); *Keiferia* spp. such as *K. lycopersicella* (tomato pinworm); *Artogeia* spp. such as *A. rapae* (imported cabbageworm); *Phthorimaea* spp. such as *P. operculella* (potato tuberworm); *Crymodes* spp. such as *C. devastator* (glassy cutworm); *Feltia* spp. such as *F. ducens* (dingy cutworm); and any combination of the foregoing.

The insecticidal proteins of the invention may also be active against Hemipteran, Dipteran, *Lygus* spp., and/or other piercing and sucking insects, for example of the order Orthoptera or Thysanoptera. Insects in the order Diptera include but are not limited to any dipteran insect now known or later identified including but not limited to *Liriomyza* spp. such as *L. trifolii* (leafminer) and *L. sativae* (vegetable leafminer); *Scrobipalpula* spp. such as *S. absoluta* (tomato leafminer); *Delia* spp. such as *D. platura* (seedcorn maggot), *D. brassicae* (cabbage maggot) and *D. radicum* (cabbage root fly); *Psilia* spp. such as *P. rosae* (carrot rust fly); *Tetanops* spp. such as *T. myopaeformis* (sugarbeet root maggot); and any combination of the foregoing.

Insects in the order Orthoptera include but are not limited to any orthopteran insect now known or later identified including but not limited to *Melanoplus* spp. such as *M. differentialis* (Differential grasshopper), *M. femurrubrum* (Redlegged grasshopper), *M. bivittatus* (Twostriped grasshopper); and any combination thereof.

Insects in the order Thysanoptera include but are not limited to any thysanopteran insect now known or later identified including but not limited to *Frankliniella* spp. such as *F. occidentalis* (western flower *thrips*) and *F. fusca* (tobacco *thrips*); and *Thrips* spp. such as *T. tabaci* (onion *thrips*), *T. palmi* (melon *thrips*); and any combination of the foregoing.

The insecticidal proteins of the invention may also be active against nematodes. The term "nematode" as used herein encompasses any organism that is now known or later identified that is classified in the animal kingdom, phylum Nematoda, including without limitation nematodes within class Adenophorea (including for example, orders Enoplida, Isolaimida, Mononchida, Dorylaimida, Trichocephalida, Mermithida, Muspiceida, Araeolaimida, Chromadorida, Desmoscolecida, Desmodorida and Monhysterida) and/or class Secernentea (including, for example, orders Rhabdita, Strongylida, Ascaridida, Spirurida, Camallanida, Diplogasterida, Tylenchida and Aphelenchida).

Nematodes include but are not limited to parasitic nematodes such as root-knot nematodes, cyst nematodes and/or lesion nematodes. Exemplary genera of nematodes according to the present invention include but are not limited to, *Meloidogyne* (root-knot nematodes), *Heterodera* (cyst nematodes), *Globodera* (cyst nematodes), *Radopholus* (burrowing nematodes), *Rotylenchulus* (reniform nematodes), *Pratylenchus* (lesion nematodes), *Aphelenchoides* (foliar nematodes), *Helicotylenchus* (spiral nematodes), *Hoplolaimus* (lance nematodes), *Paratrichodorus* (stubby-root nematodes), *Longidorus*, *Nacobbus* (false root-knot nematodes), *Subanguina*, *Belonlaimus* (sting nematodes), *Criconemella*, *Criconemoides* (ring nematodes), *Ditylenchus*, *Dolichodorus*, *Hemicriconemoides*, *Hemicycliophora*, *Hirschmaniella*, *Hypsoperine*, *Macroposthonia*, *Melinius*, *Punctodera*, *Quinisulcius*, *Scutellonema*, *Xiphinema* (dagger nematodes), *Tylenchorhynchus* (stunt nematodes), *Tylenchulus*, *Bursaphelenchus* (round worms), and any combination thereof.

Exemplary plant parasitic nematodes according to the present invention include, but are not limited to, *Belonolaimus gracilis*, *Belonolaimus longicaudatus*, *Bursaphelenchus xylophilus* (pine wood nematode), *Criconemoides ornata*, *Ditylenchus destructor* (potato rot nematode), *Ditylenchus dipsaci* (stem and bulb nematode), *Globodera pallida* (potato cyst nematode), *Globodera rostochiensis* (golden nematode), *Heterodera glycines* (soybean cyst nematode), *Heterodera schachtii* (sugar beet cyst nematode); *Heterodera zeae* (corn cyst nematode), *Heterodera avenae* (cereal cyst nematode), *Heterodera carotae*, *Heterodera trifolii*, *Hoplolaimus columbus*, *Hoplolaimus galeatus*, *Hoplolaimus magnistylus*, *Longidorus breviannulatus*, *Meloidogyne arenaria*, *Meloidogyne chitwoodi*, *Meloidogyne hapla*, *Meloidogyne incognita*, *Meloidogyne javanica*, *Mesocriconema xenoplax*, *Nacobbus aberrans*, *Naccobus dorsalis*, *Paratrichodorus christiei*, *Paratrichodorus minor*, *Pratylenchus brachyurus*, *Pratylenchus crenatus*, *Pratylenchus hexincisus*, *Pratylenchus neglectus*, *Pratylenchus penetrans*, *Pratylenchus projectus*, *Pratylenchus scribneri*, *Pratylenchus tenuicaudatus*, *Pratylenchus thornei*, *Pratylenchus zeae*, *Punctodera chaccoensis*, *Quinisulcius acutus*, *Radopholus similis*, *Rotylenchulus reniformis*, *Tylenchorhynchus dubius*, *Tylenchulus semipenetrans* (citrus nematode), *Siphinema americanum*, *X. Mediterraneum*, and any combination of the foregoing.

The invention also encompasses recombinant vectors and/or recombinant constructs, which may also be referred to as vectors or constructs, comprising the expression cassettes and/or the nucleic acid molecules of invention. In such vectors, the nucleic acids are preferably in expression cassettes comprising regulatory elements for expression of the nucleotide molecules in a host cell capable of expressing the nucleotide molecules. Such regulatory elements usually comprise promoter and termination signals and preferably also comprise elements allowing efficient translation of polypeptides encoded by the nucleic acids of the present invention. Vectors comprising the nucleic acids are capable of replication in particular host cells, preferably as extrachromosomal molecules, and are therefore used to amplify the nucleic acids of this invention in the host cells.

The invention also encompasses a host cell that comprises a recombinant vector, an expression cassette or a nucleic acid molecule of the invention. In other embodiments, such vectors are viral vectors and are used for replication of the nucleotide sequences in particular host cells, e.g. insect cells or plant cells. Recombinant vectors are also used for transformation of the nucleic acid molecules of this invention into host cells, whereby the nucleic acid molecules are stably integrated into the DNA of a transgenic host. In some embodiments, the host cell is a bacterial cell or a plant cell. In some aspects of these embodiments, the bacterial cell is in the Genus *Bacillus*, *Clostridium*, *Xenorhabdus*, *Photorhabdus*, *Pasteuria*, *Escherichia*, *Pseudomonas*, *Erwinia*, *Serratia*, *Klebsiella*, *Salmonella*, *Pasteurella*, *Xanthomonas*, *Streptomyces*, *Rhizobium*, *Sinorhizobium*, *Ensifer*, *Rhodopseudomonas*, *Methylophilius*, *Agrobacterium*, *Acetobacter*, *Lactobacillus*, *Arthrobacter*, *Azotobacter*, *Leuconostoc*, or *Alcaligenes*. *Sphingomonas*, *Burkholderia*,

*Candidatus Glomeribacter, Dyella, Herbaspirillum, Bradyrhizobium, Staphylococcus, Methylophilus, Variovorax, Streptococcus, Chitinophaga* or *Alcaligenes*. In other aspects of these embodiments, host cells for such recombinant vectors are endophytes or epiphytes. In some other aspects of these embodiments, the host cell is plant cell, for example a dicot plant cell or monocot plant cell. In other aspects, the dicot plant cell is selected from the group consisting of a soybean cell, sunflower cell, tomato cell, cole crop cell, cotton cell, sugar beet cell and tobacco cell. In still other aspects, the monocot plant cell is selected from the group consisting of a barley cell, maize cell, oat cell, rice cell, sorghum cell, sugar cane cell and wheat cell.

In some non-limiting embodiments of the invention, at least one of the nucleic acid molecules of the invention is inserted into an appropriate expression cassette, comprising a promoter and termination signal. Expression of the nucleic acid may be constitutive, or an inducible promoter responding to various types of stimuli to initiate transcription may be used. In another embodiment, the cell in which the insecticidal protein of the invention is expressed is a microorganism, such as a virus, bacteria, or a fungus. In yet another embodiment, a virus, such as a baculovirus, contains a nucleic acid of the invention in its genome and expresses large amounts of the corresponding insecticidal protein after infection of appropriate eukaryotic cells that are suitable for virus replication and expression of the nucleic acid. The insecticidal protein thus produced is used as an insecticidal agent. Alternatively, baculoviruses engineered to include the nucleic acid are used to infect insects in vivo and kill them either by expression of the insecticidal toxin or by a combination of viral infection and expression of the insecticidal toxin. In a further embodiment, the present invention also encompasses a method for producing a polypeptide with insecticidal activity, comprising culturing the host cell under conditions in which the nucleic acid molecule encoding the polypeptide is expressed.

Bacterial cells are also hosts for the expression of the nucleic acids of the invention. In one embodiment, non-pathogenic symbiotic bacteria, which are able to live and replicate within plant tissues, so-called endophytes, or non-pathogenic symbiotic bacteria, which are capable of colonizing the phyllosphere or the rhizosphere, so-called epiphytes, are used. Such bacteria include bacteria of the genera *Agrobacterium, Alcaligenes, Azospirillum, Azotobacter, Bacillus, Clavibacter, Enterobacter, Erwinia, Flavobacter, Klebsiella, Pseudomonas, Rhizobium, Sinorhizobium, Ensifer, Serratia, Streptomyces, Sphingomonas, Burkholderia, Candidatus Glomeribacter, Dyella, Herbaspirillum, Bradyrhizobium, Staphylococcus, Methylophilus, Variovorax, Streptococcus, Chitinophaga* and *Xanthomonas*. Symbiotic fungi, such as *Trichoderma* and *Gliocladium* are also possible hosts for expression of the inventive nucleic acids for the same purpose.

Techniques for these genetic manipulations are specific for the different available hosts and are known in the art. For example, the expression vectors pKK223-3 and pKK223-2 can be used to express heterologous genes in *E. coli*, either in transcriptional or translational fusion, behind the tac or trc promoter. For the expression of operons encoding multiple ORFs, the simplest procedure is to insert the operon into a vector such as pKK223-3 in transcriptional fusion, allowing the cognate ribosome binding site of the heterologous genes to be used. Techniques for overexpression in gram-positive species such as *Bacillus* are also known in the art and can be used in the context of this invention (Quax et al. In: Industrial Microorganisms: Basic and Applied Molecular Genetics, Eds. Baltz et al., American Society for Microbiology, Washington (1993)). Alternate systems for overexpression rely for example, on yeast vectors and include the use of *Pichia, Saccharomyces* and *Kluyveromyces* (Sreekrishna, In: Industrial microorganisms: basic and applied molecular genetics, Baltz, Hegeman, and Skatrud eds., American Society for Microbiology, Washington (1993); Dequin & Barre, Biotechnology L2:173-177 (1994); van den Berg et al., Biotechnology 8:135-139 (1990)).

In yet other embodiments, the invention encompasses a method of controlling insect pests, comprising delivering to the insect pests an effective insect-controlling amount of an insecticidal protein of the invention. In some aspects of these embodiments, the insecticidal protein is delivered through a transgenic plant or by topical application of an insecticidal composition comprising the insecticidal protein. In other aspects, the transgenic plant or the insecticidal composition comprises a second insecticidal agent different from the insecticidal protein. In still other aspects, the second insecticidal agent is a protein, a dsRNA or a chemical. In still other aspects, the protein is selected from the group consisting of a Cry protein, a VIP toxin, a patatin, a protease, a protease inhibitor, a urease, an alpha-amylase inhibitor, a pore-forming protein, a lectin, an engineered antibody or antibody fragment, or a chitinase; or the chemical is a carbamate, a pyrethroid, an organophosphate, a fripole, a neonicotinoid, an organochloride, a nereistoxin, or a combination thereof; or the chemical comprises an active ingredient selected from the group consisting of carbofuran, carbaryl, methomyl, bifenthrin, tefluthrin, permethrin, cyfluthrin, lambda-cyhalothrin, cypermethrin, deltamethrin, chlorpyrifos, chlorethoxyfos, dimethoate, ethoprophos, malathion, methyl-parathion, phorate, terbufos, tebupirimiphos, fipronil, acetamiprid, imidacloprid, thiacloprid, thiamethoxam, endosulfan, bensultap, and a combination thereof.

In some embodiments of the invention, at least one of the insecticidal proteins of the invention is expressed in a higher organism such as a plant. Transgenic plants expressing effective insect-controlling amounts of the insecticidal protein protect themselves from insect pest damage. When the insect pest starts feeding on such a transgenic plant, it also ingests the expressed insecticidal protein. This may deter the insect from further biting into the plant tissue and/or may even harm or kill the insect. A nucleic acid molecule of the present invention is inserted into an expression cassette, which may then be stably integrated in the genome of the plant. In other embodiments, the nucleic acid molecule is included in a non-pathogenic self-replicating virus. Plants transformed in accordance with the present invention may be monocotyledonous or dicotyledonous and include, but are not limited to, corn, wheat, oat, turfgrass, pasture grass, flax, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugar beet, sunflower, rapeseed, clover, tobacco, carrot, cotton, alfalfa, rice, potato, eggplant, cucumber, *Arabidopsis*, and woody plants such as coniferous and deciduous trees.

In some embodiments, the invention encompasses a method of producing a protein that is toxic to insect pests, i.e. an insecticidal protein, comprising: (a) obtaining a host cell comprising a gene, which itself comprises an expression cassette and/or a nucleic acid molecule of the invention; and (b) growing the transgenic host cell or a transgenic host comprising the host cell under conditions in which the host cell produces the protein that is toxic to insect pests.

In other embodiments, the invention encompasses a method of producing a transgenic plant or plant part having enhanced insect resistance compared to a control plant or plant part, comprising: (a) introducing into a plant or plant part a chimeric gene or expression cassette or vector comprising a nucleic acid molecule encoding an insecticidal protein of the invention, wherein the insecticidal protein is expressed in the plant or plant part, thereby producing a plant or plant part with enhanced insect-resistance. In other embodiments, the chimeric gene, expression cassette or vector may encode a SMIP insecticidal protein of the invention comprising, consisting essentially of or consisting of an amino acid sequence that is at least 80%, at least 85%, at least 90%, at least consisting 91%, at least 92%, at least 93%, at least 94%, at least 95%, at least 96%, at least 97%, at least 98%, or at least 99 identical or similar to any of SEQ ID NOs:1-17. "Enhanced" insect resistance may be measured as any toxic effect the transgenic plant has on the insect pest that feeds on the transgenic plant. Enhanced insect resistance may be greater than 0%, at least 1%, at least 2%, at least 3%, at least 4%, at least 5%, at least 10%, at least 15%, at least 20%, at least 25%, at least 30%, at least 40%, at least 50%, at least 60%, at least 70%, at least 80%, at least 90%, at least 100%, at least 125%, at least 150%, at least 200%, at least 300%, at least 400%, at least 500%, at least 600%, at least 700%, at least 800%, at least 900%, or at least 1000% greater insecticidal activity compared to a control plant that does not express the insecticidal protein. A plant or plant part having enhance insect resistance as compared to a control plant or plant part may be produced by methods of plant transformation, plant tissue culture, or breeding. The plant or plant part may be produced by methods of sexual or asexual propagation. Any suitable control plant or plant part can be used, for example a plant of the same or similar genetic background grown in the same environment. In embodiments, the control plant or plant part is of the same genetic background and is growing in the same environment as the described plant, but it does not comprise a molecule of the invention, while the described plant does comprise a nucleic acid molecule of the invention.

In other embodiments, the invention encompasses a method of enhancing insect resistance in a plant or plant part as compared to a control plant or plant part, comprising expressing in the plant or plant part a nucleic acid molecule or an expression cassette of the invention, wherein expression of the heterologous nucleic acid or the expression cassette results in enhanced insect resistance in a plant or plant part as compared to a control plant or plant part. In some embodiments, the expression cassette or nucleic acid molecule comprises a promoter operably linked to a heterologous nucleic acid molecule comprising a nucleotide sequence that comprises, consists essentially of or consists of (a) a nucleotide sequence of any of SEQ ID NOs:18-40; or (b) a nucleotide sequence that is at least 80%, at least 85%, at least 90%, at least 91%, at least 92%, at least 93%, at least 94%, at least 95%, at least 96%, at least 97%, at least 98%, or at least 99% identical to the nucleotide sequence of any one of SEQ ID NOs: 18-40; or (c) a nucleotide sequence that encodes a protein, wherein the amino acid sequence of the protein comprises, consists essentially of or consists of any of SEQ ID NOs:1-17; or (d) a nucleotide sequence that encodes a protein, wherein the amino acid sequence of the protein is at least 80%, at least 85%, at least 90%, at least 91%, at least 92%, at least 93%, at least 94%, at least 95%, at least 96%, at least 97%, at least 98%, or at least 99% identical to the amino acid sequence of any of SEQ ID NOs:1-17; or (e) a nucleotide sequence of any of (a) to (d) above, that is codon optimized for expression in a transgenic host organism; or (f) a nucleotide sequence that is complementary to the nucleotide sequence of any one of (a) to (e) above. The nucleic acid molecule or expression cassette may be introduced into the plant. In some embodiments, the nucleic acid molecule or expression cassette may be introduced into a plant part and a plant comprising the nucleic acid molecule or expression cassette may be produced from the plant part.

In some embodiments, the invention encompasses a method of producing a plant having enhanced insect resistance as compared to a control plant, comprising detecting, in a plant part, a heterologous nucleic acid comprising a nucleic acid molecule or an expression cassette of the invention and producing a plant from the plant part, thereby producing a plant having enhanced insect resistance as compared to a control plant. In a further embodiment, the invention encompasses a method of identifying a plant or plant part having enhanced insect resistance as compared to a control plant or plant part, comprising detecting, in the plant or plant part, a nucleic acid molecule or an expression cassette of the invention, thereby identifying a plant or plant part having enhanced insect resistance. In a further embodiment, the expression cassette or a diagnostic fragment thereof is detected in an amplification product from a nucleic acid sample from the plant or plant part. The diagnostic fragment may be a nucleic acid molecule at least 10 contiguous nucleotides long which is unique to the expression cassette of the invention.

In other embodiments, the invention encompasses a method of producing a plant having enhanced insect resistance as compared to a control plant or plant part, comprising crossing a first parent plant with a second parent plant, wherein at least the first parent plant comprises within its genome a heterologous nucleic acid that comprises a nucleic acid molecule or an expression cassette of the invention and producing a progeny generation, wherein the progeny generation comprises at least one plant that possesses the heterologous nucleic acid within its genome and that exhibits enhanced insect resistance as compared to a control plant.

In some non-limiting embodiments, the methods of the invention confer enhanced insect resistance in a plant or plant part against a coleopteran insect pest. Insect control of coleopteran insect pests are demonstrated in the Examples. In further embodiments, the methods of the invention confer enhanced insect resistance in a plant or plant part against *Diabrotica* species, including *Diabrotica virgifera virgifera, Diabrotica barberi, Diabrotica undecimpunctata howardi, Diabrotica virgifera zeae*, and/or *Diabrotica speciosa*, and/or related species. In further embodiments, the methods of the invention confer enhanced insect resistance in a plant or plant part against *Diabrotica virgifera virgifera, Diabrotica barberi*, and/or *Diabrotica undecimpunctata howardi*.

In some non-limiting embodiments, invention encompasses a transgenic plant comprising a heterologous nucleic acid molecule or an expression cassette of the invention, which when transcribed and translated confers enhanced insect resistance to the transgenic plant. In some aspects of these embodiments, the heterologous nucleic acid molecule or expression cassette comprises a nucleotide sequence that has at least 80%, at least 85%, at least 90%, at least 91% at least 92%, at least 93%, at least 94%, at least 95%, at least 96%, at least 97%, at least 98% at least 99%, or 100% identical to any of SEQ ID NOs:18-40. In other embodiments, the transgenic plant is a dicotyledonous plant or a monocotyledonous plant. In further aspects, the transgenic plant is alfalfa, apple, apricot, artichoke, arugula, asparagus, avocado, banana, beans, beet, blackberry, blueberry, broccoli, brussel sprouts, cabbage, canola, cantaloupe, carrot, cassava, cauliflower, celery, cherry, cilantro, citrus, clementine, coffee, corn, cotton, cucumber, Douglas fir, eggplant, endive, escarole, eucalyptus, fennel, figs, gourd, grape, grapefruit, honey dew, jicama, kiwifruit, lettuce, leeks, lemon, lime, Loblolly pine, mango, melon, mushroom, nut, okra, onion, orange, an ornamental plant, papaya, parsley, pea, peach, peanut, pear, pepper, persimmon, pine, pineapple, plantain, plum, pomegranate, poplar, potato, pumpkin, quince, radiata pine, radicchio, radish, raspberry, rice, rye, sorghum, Southern pine, soybean, spinach, squash, strawberry, sugarbeet, sunflower, sweet potato, sweetgum, tangerine, tea, tobacco, tomato, turf, a vine, watermelon, yams, or zucchini. In still other aspects, the transgenic plant is millet, switchgrass, maize, sorghum, wheat, oat, turf grass, pasture grass, flax, rice, sugarcane, oilseed rape, or barley.

In some non-limiting embodiments, the invention encompasses nucleic acid molecules encoding insecticidal proteins of the invention that are modified and optimized for expression in transgenic plants. Although some genes from microbial organisms can be expressed in plants at high levels without modification, low expression in transgenic plants may result from microbial nucleic acids having codons that are not preferred in plants. It is known in the art that all organisms have specific preferences for codon usage, and the codons of the nucleic acids described in this invention can be changed to conform with plant preferences, while maintaining the amino acids encoded thereby, or making certain amino acid changes to the encoded insecticidal protein. Furthermore, high expression in plants is best achieved from coding sequences that have at least about 35% GC content, preferably more than about 45%, more preferably more than about 50%, and most preferably more than about 60%. Microbial nucleic acids that have low GC contents may express poorly in plants due to the existence of ATTTA motifs that may destabilize messages, and AATAAA motifs that may cause inappropriate polyadenylation. In embodiments, sequences can be modified to account for the specific codon preferences and GC content preferences of monocotyledons or dicotyledons as these preferences have been shown to differ (Murray et al. Nucl. Acids Res. 17:477-498 (1989)). In addition, the nucleic acids are screened for the existence of illegitimate splice sites that may cause message truncation. All changes required to be made within the nucleic acids such as those described above can be made using well known techniques of site directed mutagenesis, PCR, and synthetic gene construction, for example, using the methods described in the published patent applications EP 0 385 962, EP 0 359 472, and WO 93/07278.

In some embodiments of the invention a coding sequence for an insecticidal protein of the invention is made according to the procedure disclosed in U.S. Pat. No. 5,625,136, herein incorporated by reference. In this procedure, maize preferred codons, i.e., the single codon that most frequently encodes that amino acid in maize, are used. The maize preferred codon for a particular amino acid might be derived, for example, from known gene sequences from maize. Maize codon usage for 28 genes from maize plants is found in Murray et al., Nucleic Acids Research 17:477-498 (1989), the disclosure of which is incorporated herein by reference. In this manner, the nucleotide sequences can be optimized for expression in any plant. It is recognized that all or any part of the gene sequence may be optimized or synthetic. That is, synthetic or partially optimized sequences may also be used.

For more efficient initiation of translation, sequences adjacent to the initiating methionine may be modified. For example, they can be modified by the inclusion of sequences known to be effective in plants. Joshi has suggested an appropriate consensus for plants (NAR 15:6643-6653 (1987)) and Clontech suggests a further consensus translation initiator (1993/1994 catalog, page 210). These consensus sequences are suitable for use with the nucleic acids of this invention. In embodiments, the sequences are incorporated into constructions comprising the nucleic acids, up to and including the ATG (whilst leaving the second amino acid unmodified), or alternatively up to and including the GTC subsequent to the ATG (with the possibility of modifying the second amino acid of the transgene).

Expression of the nucleic acids in transgenic plants is driven by promoters that function in plants. The choice of promoter will vary depending on the temporal and spatial requirements for expression, and also depending on the target species. Thus, expression of the nucleic acids of this invention in leaves, in stalks or stems, in ears, in inflorescences (e.g. spikes, panicles, cobs, etc.), in roots, and/or seedlings is preferred. In many cases, however, protection against more than one type of insect pest is sought, and thus expression in multiple tissues is desirable. Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the nucleic acids in the desired cell.

In some non-limiting embodiments, promoters are used that are expressed constitutively including the actin or ubiquitin or cmp promoters or the CaMV35S and 19S promoters. The nucleic acids of this invention can also be expressed under the regulation of promoters that are chemically regulated. Preferred technology for chemical induction of gene expression is detailed in the published application EP 0 332 104 (to Ciba-Geigy) and U.S. Pat. No. 5,614,395. A preferred promoter for chemical induction is the tobacco PR-1a promoter.

In other embodiments, a category of promoters which is wound inducible can be used. Numerous promoters have been described which are expressed at wound sites and also at the sites of phytopathogen infection. Ideally, such a promoter should only be active locally at the sites of infection, and in this way the insecticidal proteins of the invention only accumulate in cells that need to synthesize the proteins to kill the invading insect pest. Preferred promoters of this kind include those described by Stanford et al. Mol. Gen. Genet. 215:200-208 (1989), Xu et al. Plant Molec. Biol. 22:573-588 (1993), Logemann et al. Plant Cell 1:151-158 (1989), Rohrmeier & Lehle, Plant Molec. Biol. 22:783-792 (1993), Firek et al. Plant Molec. Biol. 22:129-142 (1993), and Warner et al. Plant J. 3:191-201 (1993).

Tissue-specific or tissue-preferential promoters useful for the expression of genes encoding insecticidal proteins of the invention in plants, particularly corn, are those which direct expression in root, pith, leaf or pollen, particularly root. Such promoters, e.g. those isolated from PEPC or trpA, are disclosed in U.S. Pat. No. 5,625,136, or MTL, disclosed in U.S. Pat. No. 5,466,785. Both U. S. patents are herein incorporated by reference in their entirety.

In addition, promoters functional in plastids can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

In some embodiments of the invention, inducible promoters can be used. Thus, for example, chemical-regulated promoters can be used to modulate the expression of nucleotide sequences of the invention in a plant through the application of an exogenous chemical regulator. Regulation of the expression of nucleotide sequences of the invention via promoters that are chemically regulated enables the polypeptides of the invention to be synthesized only when the crop plants are treated with the inducing chemicals. Depending upon the objective, the promoter may be a chemical-inducible promoter, where application of a chemical induces expression of a nucleotide sequence of the invention, or a chemical-repressible promoter, where application of the chemical represses expression of a nucleotide sequence of the invention.

Chemical inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1 a promoter, which is activated by salicylic acid (e.g., the PR1a system), steroid steroid-responsive promoters (see, e.g., the glucocorticoid-inducible promoter in Schena et al. (1991) Proc. Natl. Acad. Sci. USA 88, 10421-10425 and McNellis et al. (1998) Plant J. 14, 247-257) and tetracycline-inducible and tetracycline-repressible promoters (see, e.g., Gatz et al. (1991) Mol. Gen. Genet. 227, 229-237, and U.S. Pat. Nos. 5,814,618 and 5,789,156, Lac repressor system promoters, copper-inducible system promoters, salicylate-inducible system promoters (e.g., the PR1a system), glucocorticoid-inducible promoters (Aoyama et al. (1997) Plant J. 11:605-612), and ecdysone-inducible system promoters.

Other non-limiting examples of inducible promoters include ABA- and turgor-inducible promoters, the auxin-binding protein gene promoter (Schwob et al. (1993) Plant J. 4:423-432), the UDP glucose flavonoid glycosyl-transferase promoter (Ralston et al. (1988) Genetics 119:185-197), the MPI proteinase inhibitor promoter (Cordero et al. (1994) Plant J. 6:141-150), and the glyceraldehyde-3-phosphate dehydrogenase promoter (Kohler et al. (1995) Plant Mol. Biol. 29:1293-1298; Martinez et al. (1989) J. Mol. Biol. 208:551-565; and Quigley et al. (1989) J. Mol. Evol. 29:412-421). Also included are the benzene sulphonamide-inducible (U.S. Pat. No. 5,364,780) and alcohol-inducible (Int'l Patent Application Publication Nos. WO 97/06269 and WO 97/06268) systems and glutathione S-transferase promoters. Likewise, one can use any of the inducible promoters described in Gatz (1996) Current Opinion Biotechnol. 7:168-172 and Gatz (1997) Annu. Rev. Plant Physiol. Plant Mol. Biol. 48:89-108. Other chemically inducible promoters useful for directing the expression of the nucleotide sequences of this invention in plants are disclosed in U.S. Pat. No. 5,614,395 herein incorporated by reference in its entirety. Chemical induction of gene expression is also detailed in the published application EP 0 332 104 (to Ciba-Geigy) and U.S. Pat. No. 5,614,395. In some embodiments, a promoter for chemical induction can be the tobacco PR-1a promoter.

In further embodiments, the nucleotide sequences of the invention can be operably associated with a promoter that is wound inducible or inducible by pest or pathogen infection (e.g., a insect or nematode plant pest). Numerous promoters have been described which are expressed at wound sites and/or at the sites of pest attack (e.g., insect/nematode feeding) or phytopathogen infection. Ideally, such a promoter should be active only locally at or adjacent to the sites of attack, and in this way expression of the nucleotide sequences of the invention will be focused in the cells that are being invaded or fed upon. Such promoters include, but are not limited to, those described by Stanford et al., Mol. Gen. Genet. 215:200-208 (1989), Xu et al. Plant Molec. Biol. 22:573-588 (1993), Logemann et al. Plant Cell 1:151-158 (1989), Rohrmeier and Lehle, Plant Molec. Biol. 22:783-792 (1993), Firek et al. Plant Molec. Biol. 22:129-142 (1993), Warner et al. Plant J. 3:191-201 (1993), U.S. Pat. Nos. 5,750,386, 5,955,646, 6,262,344, 6,395,963, 6,703,541, 7,078,589, 7,196,247, 7,223,901, and U.S. Patent Application Publication 2010043102.

In some embodiments of the invention, a "minimal promoter" or "basal promoter" is used. A minimal promoter is capable of recruiting and binding RNA polymerase II complex and its accessory proteins to permit transcriptional initiation and elongation. In some embodiments, a minimal promoter is constructed to comprise only the nucleotides/nucleotide sequences from a selected promoter that are required for binding of the transcription factors and transcription of a nucleotide sequence of interest that is operably associated with the minimal promoter including but not limited to TATA box sequences. In other embodiments, the minimal promoter lacks cis sequences that recruit and bind transcription factors that modulate (e.g., enhance, repress, confer tissue specificity, confer inducibility or repressibility) transcription. A minimal promoter is generally placed upstream (i.e., 5') of a nucleotide sequence to be expressed. Thus, nucleotides/nucleotide sequences from any promoter useable with the present invention can be selected for use as a minimal promoter.

Numerous other sequences can be incorporated into expression cassettes described in this invention. These include sequences that have been shown to enhance expression such as intron sequences (e.g. from Adh1 and bronze1) and viral leader sequences (e.g. from TMV, MCMV and AMV).

It may be preferable to target expression of the nucleic acids of the present invention to different cellular localizations in the plant. In some cases, localization in the cytosol may be desirable, whereas in other cases, localization in some subcellular organelle may be preferred. Subcellular localization of transgene-encoded enzymes is undertaken using techniques well known in the art. Typically, the DNA encoding the target peptide from a known organelle-targeted gene product is manipulated and fused upstream of the nucleic acid. Many such target sequences are known for the chloroplast and their functioning in heterologous constructions has been shown. The expression of the nucleic acids of the present invention is also targeted to the endoplasmic reticulum or to the vacuoles of the host cells. Techniques to achieve this are known in the art.

Vectors suitable for plant transformation are described elsewhere in this specification. For *Agrobacterium*-mediated transformation, binary vectors or vectors carrying at least one T-DNA border sequence are suitable, whereas for direct gene transfer any vector is suitable and linear DNA containing only the construction of interest may be preferred. In the case of direct gene transfer, transformation with a single DNA species or co-transformation can be used (Schocher et al. Biotechnology 4:1093-1096 (1986)). For both direct gene transfer and *Agrobacterium*-mediated transfer, transformation is usually (but not necessarily) undertaken with a selectable marker that may provide resistance to an antibiotic (kanamycin, hygromycin or methotrexate) or a herbicide (basta). Plant transformation vectors comprising the nucleic acid molecules of the present invention may also comprise genes (e.g. phosphomannose isomerase; PMI) which provide for positive selection of the transgenic plants as disclosed in U.S. Pat. Nos. 5,767,378 and 5,994,629, herein incorporated by reference. The choice of selectable marker is not, however, critical to the invention.

In some embodiments, the nucleic acid can be transformed into the nuclear genome. In another embodiment, a nucleic acid of the present invention is directly transformed into the plastid genome. A major advantage of plastid transformation is that plastids are generally capable of expressing bacterial genes without substantial codon optimization, and plastids are capable of expressing multiple open reading frames under control of a single promoter. Plastid transformation technology is extensively described in U.S. Pat. Nos. 5,451,513, 5,545,817, and 5,545,818, in PCT application no. WO 95/16783, and in McBride et al. (1994) Proc. Nati. Acad. Sci. USA 91, 7301-7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab, Z., Hajdukiewicz, P., and Maliga, P. (1990) Proc. Nati. Acad. Sci. USA 87, 8526-8530; Staub, J. M., and Maliga, P. (1992) Plant Cell 4, 39-45). This resulted in stable homoplasmic transformants at a frequency of approximately one per 100 bombardments of target leaves. The presence of cloning sites between these markers allowed creation of a plastid targeting vector for introduction of foreign genes (Staub, J. M., and Maliga, P. (1993) EMBO J. 12, 601-606). Substantial increases in transformation frequency are obtained by replacement of the recessive rRNA or r-protein antibiotic resistance genes with a dominant selectable marker, the bacterial aadA gene encoding the spectinomycin-cletoxifying enzyme aminoglycoside-3'-adenyltransferase (Svab, Z., and Maliga, P. (1993) Proc. Natl. Acad. Sci. USA 90, 913-917). Previously, this marker had been used successfully for high-frequency transformation of the plastid genome of the green alga *Chlamydomonas reinhardtii* (Goldschmidt-Clermont, M. (1991) Nucl. Acids Res. 19:4083-4089). Other selectable markers useful for plastid transformation are known in the art and encompassed within the scope of the invention. Typically, approximately 15-20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein. In a preferred embodiment, a nucleic acid of the present invention is inserted into a plastid-targeting vector and transformed into the plastid genome of a desired plant host. Plants homoplastic for plastid genomes containing a nucleic acid of the present invention are obtained, and are preferentially capable of high expression of the nucleic acid.

In yet other embodiments, a transgenic plant of the invention may comprise a heterologous nucleic acid molecule which encodes for at least one additional desired trait. The additional trait may be encoded on the same heterologous nucleic acid molecule as a nucleic acid molecule of the invention, or it may be encoded on a second heterologous nucleic acid molecule. The additional desired trait may confer insect resistance to a second insect pest, insect resistance to the same insect pest, abiotic stress tolerance, male sterility, herbicide resistance, bacterial disease resistance, fungal disease resistance, viral disease resistance, nematode resistance, modified fatty acid metabolism, modified carbohydrate metabolism, improved nutritional value, improved performance in an industrial process or altered reproductive capability. The additional desired trait may also induce production within the plant of a commercially valuable enzyme or metabolite.

In some embodiments, the desired additional trait is a second pesticidal agent. The second pesticidal agent may be active on any plant pest, including insects, nematodes, fungi, viruses or bacteria. Examples of insect plant pests include and are not limited to *Nilaparvata* spp. (e.g. *N. lugens* (brown planthopper)); *Laodelphax* spp. (e.g. *L. striatellus* (small brown planthopper)); *Nephotettix* spp. (e.g. *N. virescens* or *N. cincticeps* (green leafhopper), or *N. nigropictus* (rice leafhopper)); *Sogatella* spp. (e.g. *S. furcifera* (whitebacked planthopper)); *Blissus* spp. (e.g. *B. leucopterus leucopterus* (chinch bug)); *Scotinophora* spp. (e.g. *S. vermidulate* (rice blackbug)); *Acrosternum* spp. (e.g. *A. hilare* (green stink bug)); *Parnara* spp. (e.g. *P. guttata* (rice skipper)); *Chilo* spp. (e.g. *C. suppressalis* (rice striped stem borer), *C. auricilius* (gold-fringed stem borer), or *C. polychrysus* (dark-headed stem borer)); *Chilotraea* spp. (e.g. *C. polychrysa* (rice stalk borer)); *Sesamia* spp. (e.g. *S. inferens* (pink rice borer)); *Tryporyza* spp. (e.g. *T. innotata* (white rice borer), or *T. incertulas* (yellow rice borer)); *Cnaphalocrocis* spp. (e.g. *C. medinalis* (rice leafroller)); *Agromyza* spp. (e.g. *A. oryzae* (leafminer), or *A. parvicornis* (corn blot leafminer)); *Diatraea* spp. (e.g. *D. saccharalis* (sugarcane borer), or *D. grandiosella* (southwestern corn borer)); *Narnaga* spp. (e.g. *N. aenescens* (green rice caterpillar)); *Xanthodes* spp. (e.g. *X. transversa* (green caterpillar)); *Spodoptera* spp. (e.g. *S. frugiperda* (fall armyworm), *S. exigua* (beet armyworm), *S. littoralis* (climbing cutworm) or *S. praefica* (western yellowstriped armyworm)); *Mythimna* spp. (e.g. *Mythmna (Pseudaletia) seperata* (armyworm)); *Helicoverpa* spp. (e.g. *H. zea* (corn earworm)); *Colaspis* spp. (e.g. *C. brunnea* (grape colaspis)); *Lissorhoptrus* spp. (e.g. *L. oryzophilus* (rice water weevil)); *Echinocnemus* spp. (e.g. *E. squamos* (rice plant weevil)); *Diclodispa* spp. (e.g. *D. armigera* (rice hispa)); *Oulema* spp. (e.g. *O. oryzae* (leaf beetle); *Sitophilus* spp. (e.g. *S. oryzae* (rice weevil)); *Pachydiplosis* spp. (e.g. *P. oryzae* (rice gall midge)); *Hydrellia* spp. (e.g. *H. griseola* (small rice leafminer), or *H. sasakii* (rice stem maggot)); *Chlorops* spp. (e.g. *C. oryzae* (stem maggot)); *Diabrotica* spp. (e.g. *D. virgifera virgifera* (western corn rootworm), *D. barberi* (northern corn rootworm), *D. undecimpunctata howardi* (southern corn rootworm), *D. virgifera zeae* (Mexican corn rootworm); *D. balteata* (banded cucumber beetle)); *Ostrinia* spp. (e.g. *O. nubilalis* (European corn borer)); *Agrotis* spp. (e.g. *A. ipsilon* (black cutworm)); *Elasmopalpus* spp. (e.g. *E. lignosellus* (lesser cornstalk borer)); *Melanotus* spp. (wireworms); *Cyclocephala* spp. (e.g. *C. borealis* (northern masked chafer), or *C. immaculata* (southern masked chafer)); *Popillia* spp. (e.g. *P. japonica* (Japanese beetle)); *Chaetocnema* spp. (e.g. *C. pulicaria* (corn flea beetle)); *Sphenophorus* spp. (e.g. *S. maidis* (maize billbug)); *Rhopalosiphum* spp. (e.g. *R. maidis* (corn leaf aphid)); *Anuraphis* spp. (e.g. *A. maidiradicis* (corn root aphid)); *Melanoplus* spp. (e.g. *M. femurrubrum* (red-legged grasshopper) *M. differentialis* (differential grasshopper) or *M. sanguinipes* (migratory grasshopper)); *Hylemya* spp. (e.g. *H. platura* (seedcorn maggot)); *Anaphothrips* spp. (e.g. *A. obscrurus* (grass *thrips*)); *Solenopsis* spp. (e.g. *S. milesta* (thief ant)); or spp. (e.g. *T. urticae* (twospotted spider mite), *T. cinnabarinus* (carmine spider mite); *Helicoverpa* spp. (e.g. *H. zea* (cotton bollworm), or *H. armigera* (American bollworm)); *Pectinophora* spp. (e.g. *P. gossypiella* (pink bollworm)); *Earias* spp. (e.g. *E. vittella* (spotted bollworm)); *Heliothis* spp. (e.g. *H. virescens* (tobacco budworm)); *Anthonomus* spp. (e.g. *A. grandis* (boll weevil)); *Pseudatomoscelis* spp. (e.g. *P. seriatus* (cotton fleahopper)); *Trialeurodes* spp. (e.g. *T. abutiloneus* (banded-winged whitefly) *T. vaporariorum* (greenhouse whitefly)); *Bemisia* spp. (e.g. *B. argentifolii* (silverleaf whitefly)); *Aphis* spp. (e.g. *A. gossypii* (cotton aphid)); *Lygus* spp. (e.g. *L. lineolaris* (tarnished plant bug) or *L. hesperus* (western tarnished plant bug)); *Euschistus* spp. (e.g. *E. conspersus* (consperse stink bug)); *Chlorochroa* spp. (e.g. *C. sayi* (Say stinkbug)); *Nezara* spp. (e.g. *N. viridula* (southern green stinkbug)); *Thrips* spp. (e.g. *T. tabaci* (onion *thrips*)); *Frankliniella* spp. (e.g. *F. fusca* (tobacco *thrips*), or *F. occidentalis* (western flower thrips)); *Leptinotarsa* spp. (e.g. *L. decemlineata* (Colorado potato beetle), *L. juncta* (false potato beetle), or *L. texana* (Texan false potato beetle)); *Lema* spp. (e.g. *L. trilineata* (three-lined potato beetle)); *Epitrix* spp. (e.g. *E. cucumeris* (potato flea beetle), *E. hirtipennis* (flea beetle), or *E. tuberis* (tuber flea beetle)); *Epicauta* spp. (e.g. *E. vittata* (striped blister beetle)); *Phaedon* spp. (e.g. *P. cochleariae* (mustard leaf beetle)); *Epilachna* spp. (e.g. *E. varivetis* (mexican bean beetle)); *Acheta* spp. (e.g. *A. domesticus* (house cricket)); *Empoasca* spp. (e.g. *E. fabae* (potato leafhopper)); *Myzus* spp. (e.g. *M. persicae* (green peach aphid)); *Paratrioza* spp. (e.g. *P. cockerelli* (psyllid)); *Conoderus* spp. (e.g. *C. falli* (southern potato wireworm), or *C. vespertinus* (tobacco wireworm)); *Phthorimaea* spp. (e.g. *P. operculella* (potato tuberworm)); *Macrosiphum* spp. (e.g. *M. euphorbiae* (potato aphid)); *Thyanta* spp. (e.g. *T. pallidovirens* (redshouldered stinkbug)); *Phthorimaea* spp. (e.g. *P. operculella* (potato tuberworm)); *Helicoverpa* spp. (e.g. *H. zea* (tomato fruitworm); *Keiferia* spp. (e.g. *K. lycopersicella* (tomato pinworm)); *Limonius* spp. (wireworms); *Manduca* spp. (e.g. *M. sexta* (tobacco hornworm), or *M. quinquemaculata* (tomato hornworm)); *Liriomyza* spp. (e.g. *L. sativae, L. trifolli* or *L. huidobrensis* (leafminer)); *Drosophilla* spp. (e.g. *D. melanogaster, D. yakuba, D. pseudoobscura* or *D. simulans*); *Carabus* spp. (e.g. *C. granulatus*); Chironomus spp. (e.g. *C. tentanus*); *Ctenocephalides* spp. (e.g. *C. felis* (cat flea)); *Diaprepes* spp. (e.g. *D. abbreviatus* (root weevil)); *Ips* spp. (e.g. *I. pini* (pine engraver)); *Tribolium* spp. (e.g. *T. castaneum* (red floor beetle)); *Glossina* spp. (e.g. *G. morsitans* (tsetse fly)); *Anopheles* spp. (e.g. *A. gambiae* (malaria mosquito)); *Helicoverpa* spp. (e.g. *H. armigera* (African Bollworm)); *Acyrthosiphon* spp. (e.g. *A. pisum* (pea aphid)); *Apis* spp. (e.g. *A. melifera* (honey bee)); *Homalodisca* spp. (e.g. *H. coagulate* (glassy-winged sharpshooter)); *Aedes* spp. (e.g. *Ae. aegypti* (yellow fever mosquito)); *Bombyx* spp. (e.g. *B. mori* (silkworm)); *Locusta* spp. (e.g. *L. migratoria* (migratory locust)); *Boophilus* spp. (e.g. *B. microplus* (cattle tick)); *Acanthoscurria* spp. (e.g. *A. gomesiana* (red-haired cholotate bird eater)); *Diploptera* spp. (e.g. *D. punctata* (pacific beetle cockroach)); *Heliconius* spp. (e.g. *H. erato* (red passion flower butterfly) or *H. melpomene* (postman butterfly)); *Curculio* spp. (e.g. *C. glandium* (acorn weevil)); *Plutella* spp. (e.g. *P. xylostella* (diamondback moth)); *Amblyomma* spp. (e.g. *A. variegatum* (cattle tick)); *Anteraea* spp. (e.g. *A. yamamai* (silkmoth)); and *Armigeres* spp. (e.g. *A. subalbatus*).

The SMIP toxins of the invention can be used in combination with other pesticidal agents to increase pest target range. Furthermore, the use of the SMIP toxins of the invention in combination with a second insecticidal agent which has a different mode of action or targets a different receptor in the insect gut has particular utility for the prevention and/or management of insect resistance. In some embodiments, a SMIP toxin of the invention is combined with a second insecticidal protein selected from the group consisting of Cry1A, Cry1Ab, Cry1Ac, Cry1A.105, Cry1Ae, Cry1B, Cry1C, Cry1C variants, Cry1D, Cry1E, Cry1F, Cry1A/F chimeras, Cry1G, Cry1H, Cry1I, Cry1J, Cry1K, Cry1L, Cry2A, Cry2Ab, Cry2Ae, Cry3, Cry3A variants, Cry3B, Cry4B, Cry6, Cry7, Cry8, Cry9, Cry15, Cry34, Cry35, Cry43A, Cry43B, Cry46A, Cry51Aa1, PtIP-96, PtIP-83, PHI-4, MP467, MP81, PS149B1, DIG-3, DIG-5, DIG-10, DIG-11, DIG-17, DIG-657, IRDIG28688.1, IRDIG28688.1, IRDIG28684.1, IRDIG28682.1, IRDIG28680.1, IRDIG28674.1, IRDIG28672.1, IRDIG27642, IRDIG28688.1, IRDIG28686.1, IRDIG28684.1, IRDIG28682.1, IRDIG28680.1, IRDIG28674.1, IRDIG28672.1, IRDIG27642, IRDIG28678.2, IRDIG28678.1, IRDIG31125.1, IRDIG28696.1, IRDIG29781.1, IRDIG29779.1, IRDIG30844.1, IRDIG30850.1, IRDIG30852.1, IRDIG30854.1, IRDIG30856.1, IRDIG30858.1, IRDIG30862.1, IRDIG30860.1, IRDIG30848.1, RETIRE2021, VIP3A, VIP3B, VIP3Ab, the binary VIP1 and VIP2, or other vegetative insecticidal protein, mCry3A, eCry3.1Ab, AXMI-001, AXMI-002, AXMI-030, AXMI-035, AXMI-036, AXMI-045, AXMI52, AXMI58, AXMI88, AXM197, AXMI102, AXMI112, AXMI113, AXMI115, AXMI117, AXMI100, AXMI-115, AXMI-113, and AXMI-005, AXMI134, AXMI-150, AXMI171, AXMI-184, AXMI196, AXMI204, AXMI207, AXMI209, AXMI205, AXMI218, AXMI220, AXMI221z, AXMI222z, AXMI223z, AXMI224z and AXMI225z, AXMI238, AXMI270, AXMI279, AXMI345, AXMI-R1 and variants thereof, IP3 and variants thereof, ET29, ET33, ET34, ET35, ET66, ET70, TIC400, TIC407, TIC417, TIC431, TIC800, TIC807, TIC834, TIC836, TIC844, TIC853, TIC860 or variant thereof, TIC867 or variant thereof, TIC868 or variant thereof, TIC869, TIC900 or related protein, TIC901, TIC1100, TIC1201, TIC1362, TIC1414, TIC1415, TIC1422, TIC1497, TIC1498, TIC1885, TIC1886, TIC1922, TIC1925, TIC1974, TIC2032, TIC2120, TIC2160, TIC3131, TIC3244, TIC6757, TIC7243, TIC7472, and a TIC7473 protein, or hybrid proteins or chimeras made from any of the preceding insecticidal proteins. The second insecticidal agent can also be an agent selected from the group comprising an a amylase, a peroxidase, a cholesterol oxidase, a patatin, a protease, a protease inhibitor, a urease, an alpha-amylase inhibitor, a pore-forming protein, a chitinase, a lectin, an engineered antibody or antibody fragment, a *Bacillus cereus* insecticidal protein, a *Xenorhabdus* spp. (such as *X. nematophila* or *X. bovienii*) insecticidal protein, a *Photorhabdus* spp. (such as *P. luminescens* or *P. asymobiotica*) insecticidal protein, a *Breviba-*

*cillus* spp. (such as *B. laterosporous*) insecticidal protein, a *Lysinibacillus* spp. (such as *L. sphearicus*) insecticidal protein, a *Chromobacterium* spp. (such as *C. subtsugae* or *C. piscinae*) insecticidal protein, a *Yersinia* spp. (such as *Y. entomophaga*) insecticidal protein, a *Paenibacillus* spp. (such as *P. propylaea*) insecticidal protein, a *Clostridium* spp. (such as *C. bifermentans*) insecticidal protein, and a lignin. In other embodiments, the second agent may be at least one insecticidal protein derived from an insecticidal toxin complex (Tc) from *Photorhabdus, Xenorhabus, Serratia*, or *Yersinia*. In still other embodiments, the second insecticidal protein may be a binary toxin derived from an insecticidal bacteria, such as ISP1A and ISP2A from *B. laterosporous* or BinA and BinB from *L. sphaericus*. The combination of a SMIP toxin of the invention and a second pesticidal agent may be through expression of both proteins in a transgenic plant. In some embodiments the transgenic plant is a transgenic corn plant. In other embodiments, the combination in the transgenic corn plant is a SMIP toxin of the invention and mCry3A and/or eCry3.1Ab and/or Cry3Bb1 and/or Cry34/Cry35.

In some embodiments, the transgenic plant of the invention may comprise at least a second pesticidal agent which is non-proteinaceous. In preferred embodiments, the second pesticidal agent is an interfering RNA molecule. An interfering RNA typically comprises at least a RNA fragment against a target gene, a spacer sequence, and a second RNA fragment which is complementary to the first, so that a double-stranded RNA structure can be formed. RNA interference (RNAi) occurs when an organism recognizes double-stranded RNA (dsRNA) molecules and hydrolyzes them. The resulting hydrolysis products are small RNA fragments of about 19-24 nucleotides in length, called small interfering RNAs (siRNAs). The siRNAs then diffuse or are carried throughout the organism, including across cellular membranes, where they hybridize to mRNAs (or other RNAs) and cause hydrolysis of the RNA. Interfering RNAs are recognized by the RNA interference silencing complex (RISC) into which an effector strand (or "guide strand") of the RNA is loaded. This guide strand acts as a template for the recognition and destruction of the duplex sequences. This process is repeated each time the siRNA hybridizes to its complementary-RNA target, effectively preventing those mRNAs from being translated, and thus "silencing" the expression of specific genes from which the mRNAs were transcribed. Interfering RNAs are known in the art to be useful for insect control (see, for example, publication WO2013/192256, incorporated by reference herein). An interfering RNA designed for use in insect control produces a non-naturally occurring double-stranded RNA, which takes advantage of the native RNAi pathways in the insect to trigger down-regulation of target genes that may lead to the cessation of feeding and/or growth and may result in the death of the insect pest. The interfering RNA molecule may confer insect resistance against the same target pest as the protein of the invention, or may target a different pest. The targeted insect plant pest may feed by chewing, sucking, or piercing. Interfering RNAs are known in the art to be useful for insect control. In other embodiments, the interfering RNA may confer resistance against a non-insect plant pest, such as a nematode pest or a virus pest.

The co-expression of more than one pesticidal agent in the same transgenic plant can be achieved by making a single recombinant vector comprising coding sequences of more than one pesticidal agent in a so called molecular stack and genetically engineering a plant to contain and express all the pesticidal agents in the transgenic plant. Such molecular stacks may be also be made by using mini-chromosomes as described, for example in U.S. Pat. No. 7,235,716. Alternatively, a transgenic plant comprising one nucleic acid encoding a first pesticidal agent can be re-transformed with a different nucleic acid encoding a second pesticidal agent and so forth. Alternatively, a plant, Parent 1, can be genetically engineered for the expression of genes of the present invention. A second plant, Parent 2, can be genetically engineered for the expression of a second pesticidal agent. By crossing Parent 1 with Parent 2, progeny plants are obtained which express all the genes introduced into Parents 1 and 2.

Transgenic plants or seed comprising an insecticidal protein of the invention can also be treated with an insecticide or insecticidal seed coating as described in U.S. Pat. Nos. 5,849,320 and 5,876,739, herein incorporated by reference. Where both the insecticide or insecticidal seed coating and the transgenic plant or seed of the invention are active against the same target insect, for example a Coleopteran pest or a *Diabrotica* target pest, the combination is useful (i) in a method for further enhancing activity of the composition of the invention against the target insect, and (ii) in a method for preventing development of resistance to the composition of the invention by providing yet another mechanism of action against the target insect. Thus, the invention provides a method of enhancing control of a *Diabrotica* insect population comprising providing a transgenic plant or seed of the invention and applying to the plant or the seed an insecticide or insecticidal seed coating to a transgenic plant or seed of the invention.

Even where the insecticidal seed coating is active against a different insect, the insecticidal seed coating is useful to expand the range of insect control, for example by adding an insecticidal seed coating that has activity against lepidopteran insects to a transgenic seed of the invention, which, in some embodiments, has activity against coleopteran and some lepidopteran insects, the coated transgenic seed produced controls both lepidopteran and coleopteran insect pests.

Examples of such insecticides and/or insecticidal seed coatings include, without limitation, a carbamate, a pyrethroid, an organophosphate, a friprole, a neonicotinoid, an organochloride, a nereistoxin, or a combination thereof. In another embodiment, the insecticide or insecticidal seed coating are selected from the group consisting of carbofuran, carbaryl, methomyl, bifenthrin, tefluthrin, permethrin, cyfluthrin, lambda-cyhalothrin, cypermethrin, deltamethrin, chlorpyrifos, chlorethoxyfos, dimethoate, ethoprophos, malathion, methyl-parathion, phorate, terbufos, tebupirimiphos, fipronil, acetamiprid, imidacloprid, thiacloprid, thiamethoxam, endosulfan, bensultap, and a combination thereof. Commercial products containing such insecticides and insecticidal seed coatings include, without limitation, Furadan® (carbofuran), Lanate® (methomyl, metomil, mesomile), Sevin® (carbaryl), Talstar® (bifenthrin), Force® (tefluthrin), Ammo® (cypermethrin), Cymbush® (cypermethrin), Delta Gold® (deltamethrin), Karate® (lambda-cyhalothrin), Ambush® (permethrin), Pounce® (permethrin), Brigade® (bifenthrin), Capture® (bifenthrin), ProShield® (tefluthrin), Warrior® (lambda-cyhalothrin), Dursban® (chlorphyrifos), Fortress® (chlorethoxyfos), Mocap® (ethoprop), Thimet® (phorate), AAstar® (phorate, flucythinate), Rampart® (phorate), Counter® (terbufos), Cygon® (dimethoate), Dicapthon, Regent® (fipronil), Cruiser® (thiamethoxam), Gaucho® (imidacloprid), Prescribe® (imidacloprid), Poncho® (clothianidin) and Aztec® (cyfluthrin, tebupirimphos).

In some embodiments, the invention also encompasses a composition comprising an effective insect-controlling amount of an insecticidal protein of the invention. In further embodiments, the composition comprises a suitable agricultural carrier and an insecticidal protein of the invention. The agricultural carrier may include adjuvants, mixers, enhancers, etc. beneficial for application of an active ingredient, such as a protein of the invention, including a protein comprising, consisting essentially of or consisting of an amino acid sequence that is at least 80%, at least 85%, at least 90%, at least 95%, or 100% identical to of any of SEQ ID NO:1-17. Suitable carriers should not be phytotoxic to valuable crops, particularly at the concentrations employed in applying the compositions in the presence of crops, and should not react chemically with the compounds of the active ingredient herein, namely a polypeptide of the invention, or other composition ingredients. Such mixtures can be designed for application directly to crops, or can be concentrates or formulations which are normally diluted with additional carriers and adjuvants before application. They may include inert or active components and can be solids, such as, for example, dusts, powders, granules, water dispersible granules, or wettable powders, or liquids, for example, emulsifiable concentrates, solutions, emulsions or suspensions. Suitable agricultural carriers may include liquid carriers, for example water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, and the like. Water is generally the carrier of choice for the dilution of concentrates. Suitable solid carriers may include talc, pyrophyllite clay, silica, attapulgus clay, kieselguhr, chalk, diatomaceous earth, lime, calcium carbonate, bentonire clay, Fuller's earth, cotton seed hulls, wheat flour, soybean flour, pumice, wood flour, walnut shell flour, lignin, and the like. In other embodiments, a protein of the invention may be encapsulated in a synthetic matrix such as a polymer and applied to the surface of a host such as a plant. Ingestion of the host cells by an insect permits delivery of the insect control agents to the insect and results in a toxic effect in the insect pest.

In further embodiments, a composition of the invention may be a powder, dust, pellet, granule, spray, emulsion, colloid, or solution. A composition of the invention may be prepared by desiccation, lyophilization, homogenization, extraction, filtration, centrifugation, sedimentation, or concentration of a culture of bacterial cells. A composition of the invention may comprise at least 1%, about 5%, at least 10%, at least 20%, at least 25%, at least 30%, at least 35%, at least 40%, at least 50%, at least 60%, at least 70%, at least 80%, at least 90%, at least 95%, at least 97%, or at least 99% by weight a polypeptide of the invention. A composition of the invention may comprise at least a second pesticidal agent, which may be insecticidal, nematicidal, fungicidal, or bactericidal. At least a second pesticidal agent may be insecticidal to the same insect as a polypeptide of the invention or to a different insect. The second pesticidal agent may be a polypeptide. The pesticidal agent may be an interfering RNA. The second pesticidal agent may be a microorganism, such as a bacteria, which comprises a nucleic acid molecule that encodes for a pesticidal agent and/or contains a pesticidal agent such as a polypeptide or interfering RNA. The microorganism may be attenuated, heat-inactivated, or lyophilized. The microorganism may be dead or unable to reproduce. The second pesticidal agent may be an insecticide, for example arbofuran, carbaryl, methomyl, bifenthrin, tefluthrin, permethrin, cyfluthrin, lambda-cyhalothrin, cypermethrin, deltamethrin, chlorpyrifos, chlorethoxyfos, dimethoate, ethoprophos, malathion, methyl-parathion, phorate, terbufos, tebupirimiphos, fipronil, acetamiprid, imidacloprid, thiacloprid, thiamethoxam, endosulfan, bensultap, or a combination thereof, or a commercial product containing such insecticides and insecticidal seed coatings as described above.

A composition of the invention, for example a composition comprising a protein of the invention and an agriculturally acceptable carrier, may be used in conventional agricultural methods. An agriculturally acceptable carrier is a formulation useful for applying a composition comprising a polypeptide of the invention to a plant or seed. For example, the compositions of the invention may be mixed with water and/or fertilizers and may be applied pre-emergence and/or post-emergence to a desired locus by any means, such as airplane spray tanks, irrigation equipment, direct injection spray equipment, knapsack spray tanks, cattle dipping vats, farm equipment used in ground spraying (e.g., boom sprayers, hand sprayers), and the like. The desired locus may be soil, plants, and the like.

A composition of the invention may be applied to a seed or plant propagule in any physiological state, at any time between harvest of the seed and sowing of the seed; during or after sowing; and/or after sprouting. It is preferred that the seed or plant propagule be in a sufficiently durable state that it incurs no or minimal damage, including physical damage or biological damage, during the treatment process. A formulation may be applied to the seeds or plant propagules using conventional coating techniques and machines, such as fluidized bed techniques, the roller mill method, rotostatic seed treaters, and drum coaters.

In some embodiments, the invention also comprises a method for controlling a coleopteran pest population comprising contacting the pest population with an effective insect-controlling amount of an insecticidal protein of the invention, where the protein comprises, consist essentially of or consists of an amino acid sequence that has at least 80%, at least 85%, at least 90%, at least 91%, at least 92%, at least 93%, at least 94%, at least 95%, at least 96%, at least 97%, at least 98%, at least 99%, or is 100% identical to any one of SEQ ID NO:1-17. Contacting includes members of the pest population feeding on or ingesting the insecticidal protein. The insecticidal protein may be incorporated into insect diet food or may be expressed in or present on plant tissue which the insect population then ingests. In further embodiments, controlling the coleopteran pest population includes killing the insects by contacting the insects with an effective insect-controlling amount of an insecticidal protein of the invention.

The present invention also comprises a method for increasing yield in a plant comprising growing in a field a plant, or a seed thereof, having stably incorporated into its genome a nucleic acid molecule of an expression cassette of the invention, and wherein said field is infested with a pest against which said polypeptide has insecticidal activity.

Once a desired nucleic acid has been transformed into a particular plant species, it may be propagated in that species or moved into other varieties of the same species, particularly including commercial varieties, using traditional breeding techniques.

In some embodiments, the invention encompasses a method of providing a corn grower with a means of controlling a *Diabrotica* insect pest population in a corn crop comprising (a) selling or providing to the grower transgenic corn seed that comprises a nucleic acid molecule, an expression cassette, a vector or a chimeric gene of the invention; and (b) advertising to the grower that the transgenic corn seed produce transgenic corn plants that control a *Diabrotica* pest population.

In some embodiments, the invention also encompasses a method of identifying an insecticidal protein comprising, consisting essentially of or consisting of a nucleotide sequence having has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or having 100% sequence identity with any of SEQ ID NOs:1-17, or a toxin fragment thereof, the method comprising the steps of: (a) producing a primer pair that will amplify a polynucleotide of any of SEQ ID NOs:18-40 from a nucleic acid sample, or a complement thereof, (b) amplifying an orthologous polynucleotide from the nucleic acid sample, (c) identifying a nucleotide sequence of an orthologous polynucleotide, (d) producing a protein encoded by the orthologous polynucleotide, and (e) determining that the protein of step (d) has insecticidal activity against an insect pest.

EXAMPLES

Embodiments of this invention can be better understood by reference to the following examples. The foregoing and following description of embodiments of the invention and the various embodiments are not intended to limit the claims, but are rather illustrative thereof. Therefore, it will be understood that the claims are not limited to the specific details of these examples. It will be appreciated by those skilled in the art that other embodiments of the invention may be practiced without departing from the spirit and the scope of the disclosure, the scope of which is defined by the appended claims. Art recognized recombinant DNA and molecular cloning techniques may be found in, for example, J. Sambrook, et al., Molecular Cloning: *A Laboratory Manual*, 3d Ed., Cold Spring Harbor, NY: Cold Spring Harbor Laboratory Press (2001); by T. J. Silhavy, M. L. Berman, and L. W. Enquist, *Experiments with Gene Fusions*, Cold Spring Harbor Laboratory, Cold Spring Harbor, NY (1984) and by Ausubel, F. M. et al., *Current Protocols in Molecular Biology*, New York, John Wiley and Sons Inc., (1988), Reiter, et al., *Methods in Arabidopsis Research*, World Scientific Press (1992), and Schultz et al., *Plant Molecular Biology Manual*, Kluwer Academic Publishers (1998).

Example 1: Identification of Insecticidal Proteins

Based on proprietary algorithms, candidate nucleotide sequences encoding proteins, described in the art as hypothetical proteins, were identified in the genomes of gram negative bacteria, which belong to the family Actinomycetaceae. Two candidate sequences were chosen for expression and testing against insect pests. The two candidate nucleotide sequences were identified in the genomes of a *Streptomyces* sp. strain F-5053 (SEQ ID NO:18) and a *Streptomyces* sp. strain 8K308 (SEQ ID NO: 19). Surprisingly, a protein comprising the amino acid sequence of SEQ ID NO: 1 encoded by SEQ ID NO:18 and a protein comprising the amino acid sequence of SEQ ID NO:17 encoded by SEQ ID NO:19, were found to have insecticidal activity against western corn rootworm (WCR; *Diabrotica virgifera virgifera*). An *Escherichia coli* codon-optimized version of the F-5053 and the 8K308 nucleotide sequences were produced, SEQ ID NO:20 and SEQ ID NO:36, respectively, and each separately introduced into a pET29a bacterial expression vector to generate protein referred to as pET-Strept5053 and pET-Strept8K308, respectively. The constructs were transformed into *E. coli* BL21*(DE3) and a lysate was made from isopropyl β-D-1-thiogalactopyranoside (IPTG)-induced cultures with protein production at about 18° C. overnight. Lysates were tested for insecticidal activity against WCR in a diet-incorporation bioassay experiment. Briefly, *E. coli* lysates were mixed with an equal volume of heated artificial insect diet (Bioserv, Inc., Frenchtown, NJ) in 1.5 mL centrifuge tubes and then applied to small petri-dishes. After the diet-sample mixture cooled and solidified, 12 WCR larvae were added to each plate. The plates were sealed and maintained at ambient laboratory conditions with regard to temperature, lighting and relative humidity. Buffer without lysate, lysates from *E. coli* BL21*(DE3) cultures harboring the empty pET29a vector, and artificial insect diet alone were used as negative controls. Results are shown in Table 1. Observations regarding percent mortality and growth inhibition, where s=small larvae, m=medium larvae and l=large larvae, were taken at 4 and 7 days post-infestation.

TABLE 1

Insecticidal activity of Streptomyces proteins against WCR.

| Treatment | Day 4 | | Day 7 | |
| --- | --- | --- | --- | --- |
| | % Mortality | Growth | % Mortality | Growth |
| 50 mM Tris 8.5, 50 mM NaCl | 0 | m | 0 | l |
| BL21*/pET29a-empty | 33 | l | 33 | l |
| Diet alone | 0 | l | 0 | l |
| BL21*/pET-Strept5053 | 33 | m | 100 | — |
| BL21*/pET-Strept8K308 | 100 | — | 100 | — |

As shown in Table 1, lysate from an *E. coli* culture expressing a *Streptomyces* sp. F-5053 protein (SEQ ID NO:1) or a *Streptomyces* sp. 8K308 protein (SEQ ID NO:17) was insecticidal to western corn rootworm, *Diabrotica virgifera virgifera*. The *Streptomyces* sp. F-5053 insecticidal protein was designated Strept5053CRW or SMIP1Aa and the *Streptomyces* sp. 8K308 protein was designated Strept8K308CR W or SMIP2Aa. SMIP1Aa has 118 amino acids, is 12.8 kDa and comprises an aegerolysin-like pore forming domain from about amino acid position 20 to about amino acid position 82 of SEQ ID NO:1. The SMIP2Aa has 150 amino acids, is 16.2 kDa and comprises an aegerolysin-like pore forming domain from about amino acid position 52 to about amino acid position 114 of SEQ ID NO:17. The SMIP2Aa protein appears to have an N-terminal peptide extension of 32 amino acids (amino acids 1-32 of SEQ ID NO:17) compared to the SMIP1Aa. The apparent core toxin of the SMIP2Aa protein, i.e. a fragment comprising amino acids 33 to 150 of SEQ ID NO:17, has 71% identity to SEQ ID NO:1 as shown in the alignment in Table 2, where a "." indicates the same amino acid at that aligned position.

TABLE 2

Alignment of SMIP1Aa and SMIP2Aa.

| Pos | Sequence | Start | End | Length | Matches | % Identity |
|---|---|---|---|---|---|---|
| Ref 1 | SMIP1Aa (SEQ ID NO: 1) | 1 | 118 | 118 aa | | |
| 2 | SMIP2Aa (SEQ ID NO: 17) | 33 | 150 | 118 aa | 84 | 71 |

```
SMIP1Aa    1 maarsyeiaivnltdveftrkeahldhgvwskdgnytppdkistgqtahf
SMIP2Aa   33 ......d.s.....nm.l..eks........ge.se......ap.e.v..

SMIP1Aa   51 gsesqgvatgteghviysssagdfrvdwdnpyiggdsssakcppsyekvl
SMIP2Aa   83 ......fm.....y.t.g.p....t.y.....v.s.....t..sg....k SMIP1Aa  101 sdskgndatlkvvfykks
SMIP2Aa  133 ...a..n........en.
```

Example 2. Fate of SMIPs in Simulated Gastric Fluid Assay

Results of experiments testing SMIP1Aa and SMIP2Aa in a Simulated Gastric Fluid (SGF) assay demonstrated that the native insecticidal proteins comprising the amino acid sequence of SEQ ID NO: 1 or SEQ ID NO:17 was delayed in being fully digested, with an undigested band still present at about the 30 minute time period. The SGF assay is used to approximate the digestion of the protein in the mammalian gut, and is a standard component of the evaluation of any new insecticidal protein for regulatory approval. Therefore, SMIP1Aa mutants were made and then tested in SGF assays to determine their digestibility.

Mutants were made by making single or double amino acid substitutions in the native SMIP1Aa sequence (SEQ ID NO:1). The mutants that were made included the following: the A71 residue was changed to L (SMIP1Aa-A71L; SEQ ID NO:2), the A90 residue was changed to L (SMIP1Aa-A90L; SEQ ID NO:3), the C92 residue was changed to L or S (SMIP1Aa-C92L; SEQ ID NO:4 and SMIP1Aa-C92S; SEQ ID NO:5), the G84 residue was changed to L (SMIP1Aa-G84L; SEQ ID NO:6), the G85 residue was changed to L (SMIP1Aa-G85L; SEQ ID NO:7), the V76 residue was changed to L (SMIP1Aa-V76L; SEQ ID NO:8), the W78 residue was changed to F (SMIP1Aa-W78F; SEQ ID NO:9), the A71 and the A90 residues were both changed to L (SMIP1Aa-A71L/A90L; SEQ ID NO:10), the A71 and W78 residues were changed to L and F, respectively (SMIP1Aa-A71L/W78F; SEQ ID NO:11), the W78 and the C92 residues were changed to F and L respectively (SMIP1Aa-W78F/C92L; SEQ ID NO:12), the Y82 and the 183 residues were changed to F and L respectively (SMIP1Aa-Y82F/183L; SEQ ID NO:13) and the A2 and A3 residues were both changed to G (SMIP1Aa-A2G/A3G; SEQ ID NO:14) or V (SMIP1Aa-A2V/A3V; SEQ ID NO:15).

A simulated gastric fluid (SGF) assay measures the in vitro digestibility of a test protein at tightly controlled conditions representative of the upper mammalian digestive tract. In brief, bacterially produced test SMIP1Aa protein and mutants (at a concentration of 0.5-5 mg/ml) were exposed to the enzyme pepsin (from porcine gastric mucosa, solubilized in 2 mg/ml NaCl, pH 1.2) at a ratio of 10 Units of pepsin activity/µg test protein over a time period of one hour at 37° C. Samples are removed at 1, 2, 5, 10, 30, and 60 minutes and immediately quenched with the addition of pre-heated (95° C.-2 minutes) stop buffer (65% 0.5M Sodium Bicarbonate pH 11, 35% Tricine Loading Buffer) to immediately render pepsin inactive, and returned to heat for an additional 5 minutes. Once the assay was complete, time point samples and controls (test protein alone, pepsin alone) were examined by SDS-PAGE on a 10-20% Tris-Tricine gel (with peptides visible down to 1 kDa) to track the kinetics and level of digestion performed by pepsin.

The results of the SGF assay demonstrated that the mutants SMIP1Aa-A71L/A90L (SEQ ID NO:10) and SMIP1Aa-W78F/C92L (SEQ ID NO:12) degraded very rapidly compared with the wild-type SMIP1Aa protein. Although the mutants SMIP1Aa-A71L (SEQ ID NO:2), SMIP1Aa-A90L (SEQ ID NO:3), SMIP1Aa-C92S (SEQ ID NO:5) and SMIP1Aa-W78F (SEQ ID NO:9) were not completely degraded, they did show a significant improvement in digestibility compared with the wild-type SMIP1Aa protein. The digestibility of the mutants SMIP1Aa-C92L (SEQ ID NO:4), SMIP1Aa-G85L (SEQ ID NO:7), SMIP1Aa-V76L (SEQ ID NO:8) and SMIP1Aa-Y82F 183L (SEQ ID NO:13) was no different under these SGF conditions from the wild-type SMIP1Aa protein.

These results provide evidence that Streptomyces Insecticidal Proteins (SMIPs) of the invention can be mutated to improve digestibility in standard SGF assays.

Example 3. Solubility and Insecticidal Activity of SMIP Variants Against WCR SMIP1Aa mutants described above were tested for solubility and insecticidal activity against western corn rootworm (WCR) in a diet-incorporation bioassay experiment similar to that described in Example 1. Results of the bioassays are shown in Tables 3 to 6. Percent mortality and growth inhibition observations, where s=small larvae, m=medium larvae and l=large larvae, were taken at 3, 4 and/or 6 days post-infestation. All mutants were highly soluble except SMIP1Aa-A71L/W78F (SEQ ID NO:11), which had very low solubility.

TABLE 3

Insecticidal activity of SMIP1Aa mutants against WCR.

| Treatment | Day 3 | | Day 6 | |
|---|---|---|---|---|
| (Concentration) | % Mort | Growth | % Mort. | Growth |
| pET29a-empty (1:50) | 25 | ml | 33 | l |
| SMIP1Aa-A71L (1:50) | 83 | m | 100 | |
| SMIP1Aa-V76L (1:50) | 83 | m | 100 | |
| SMIP1Aa-G84L (1:50) | 25 | ml | 42 | ml |
| SMIP1Aa-G85L (1:50) | 75 | ml | 100 | |
| SMIP1Aa-A90L (1:50) | 100 | | 100 | |

TABLE 3-continued

Insecticidal activity of SMIP1Aa mutants against WCR.

| Treatment (Concentration) | Day 3 % Mort | Day 3 Growth | Day 6 % Mort. | Day 6 Growth |
|---|---|---|---|---|
| SMIP1Aa-W78F (1:50) | 100 | | 100 | |
| SMIP1Aa-C92S (1:40) | 83 | | | |
| Smip1Aa-C92L (1:40) | 75 | | | |
| SMIP1Aa0W78F (1:40) | 92 | | | |
| SMIP1AaY82F/I83L (1:40) | 58 | | | |

TABLE 4

Insecticidal activity of SMIP1Aa-A71L mutant against WCR.

| Treatment (Concentration) | Day 3 % Mort | Day 3 Growth | Day 6 % Mort. | Day 6 Growth |
|---|---|---|---|---|
| SMIP1Aa-A71L (200 g/ml) | 17 | sm | 100 | |
| SMIP1Aa-A71L (100 µg/ml) | 0 | ml | 92 | ml |
| SMIP1Aa-A71L (50 µgm/l) | 0 | ml | 58 | ml |
| SMIP1Aa-A71L (25 µg/ml) | 0 | ml | 33 | l |
| SMIP1Aa-A71L (12.5 µg/ml) | 8 | ml | 50 | l |
| 1X PBS | 0 | ml | 0 | l |
| 1X PBS | 0 | ml | 8 | l |

TABLE 5

Insecticidal activity of SMIP1Aa-A2G/A3G mutant against WCR.

| Treatment (Concentration) | Day 3 % Mort | Day 3 Growth | Day 6 % Mort. | Day 6 Growth |
|---|---|---|---|---|
| SMIP1Aa-A2G/A3G (375 µg/ml) | 83 | | 100 | |
| SMIP1Aa-A2V/A3V (375 µg/ml) | 75 | | 100 | |
| SMIP1Aa-A2G/A3G (250 µg/ml) | 75 | | 100 | |
| SMIP1Aa-A2V/A3V (250 µg/ml) | 58 | | 92 | m |
| SMIP1Aa-A2G/A3G (125 µg/ml) | 50 | | 92 | s |
| SMIP1Aa-A2V/A3V (125 µg/ml) | 75 | | 100 | |
| SMIP1Aa-A2G/A3G (63 µg/ml) | 58 | | 100 | |
| SMIP1Aa-A2V/A3V (63 µg/ml) | 17 | | 75 | m |
| pET29a-empty | 0 | | 0 | l |
| 50 mM Kpi pH7.0, 50 mM NaCl | 0 | | 0 | l |

TABLE 6

Insecticidal activity of SMIP1Aa - 78F/C92L and -A71L/A90L mutants against WCR.

| Treatment (Concentration) | Day 4 % Mort | Day 4 Growth | Day 6 % Mort. | Day 6 Growth |
|---|---|---|---|---|
| SMIP1Aa-W78F/C92L (200 µg/ml) | 58 | m | 100 | |
| SMIP1Aa-W78F/C92L (200 µg/ml) | 75 | sm | 100 | |
| SMIP1Aa-W78F/C92L (100 µg/ml) | 58 | m | 92 | l |
| SMIP1Aa-W78F/C92L (100 µg/ml) | 58 | m | 100 | |
| SMIP1Aa-W78F/C92L (50 µg/ml) | 67 | ml | 100 | |
| SMIP1Aa-W78F/C92L (50 µg/ml) | 50 | ml | 75 | ml; |
| SMIP1Aa-W78F/C92L (25 µg/ml) | 25 | ml | 58 | m |
| SMIP1Aa-W78F/C92L (25 µg/ml) | 17 | ml | 92 | m |
| SMIP1Aa-W78F/C92L (12.5 µg/ml) | 8 | l | 17 | l |
| SMIP1Aa-W78F/C92L (12.5 µg/ml) | 17 | l | 42 | l |
| SMIP1Aa-A71L/A90L (200 µg/ml) | 25 | ml | 92 | m |
| SMIP1Aa-A71L/A90L (200 µg/ml) | 42 | ml | 92 | m |
| SMIP1Aa-A71L/A90L (100 µg/ml) | 17 | l | 25 | ml |
| SMIP1Aa-A71L/A90L (100 µg/ml) | 17 | l | 25 | |
| SMIP1Aa-A71L/A90L (50 µg/ml) | 17 | l | 42 | l |
| SMIP1Aa-A71L/A90L (50 µg/ml) | 25 | l | 42 | ml |
| SMIP1Aa-A71L/A90L (25 µg/ml) | 0 | l | 8 | l |

TABLE 6-continued

Insecticidal activity of SMIP1Aa - 78F/C92L and -A71L/A90L mutants against WCR.

| Treatment (Concentration) | Day 4 % Mort | Day 4 Growth | Day 6 % Mort. | Day 6 Growth |
|---|---|---|---|---|
| SMIP1Aa-A71L/A90L (25 µg/ml) | 17 | 1 | 25 | 1 |
| SMIP1Aa-A71L/A90L (12.5 µg/ml) | 8 | 1 | 8 | 1 |
| SMIP1Aa-A71L/A90L (12.5 µg/ml) | 8 | 1 | 33 | 1 |
| 1X PBS | 0 | 1 | 0 | 1 |
| 1X PBS | 8 | 1 | 25 | 1 |

Example 4. Insecticidal Activity of SMIP1Aa Against Cry-Resistant WCR

To determine if SMIP toxicity is through a mode-of-action different from Cry3-related proteins, SUMO labelled SMIP1Aa and a SIMP1Aa-W78F/C92L variant were purified as in Example 2 and were tested for efficacy against a strain of WCR that is resistant to a modified Cry3A (mCry3A) toxin (mCry3A-R) and/or against a strain of WCR that is resistant to an eCry3.1Ab toxin (eCry3.1Ab-R). Diet-incorporation assays were performed essentially as described in Example 2, and mortality and growth inhibition observations, where s=small larvae, m=medium larvae and l=large larvae, were taken on days 4 and/or 6 post-infestation. SMIP1Aa and SMIP1Aa-W78F/C92L were tested at different concentrations. The negative control consisted of 1×PBS. A WCR strain that is not resistant to mCry3A or eCry3.1Ab, i.e. wild-type was used as a positive control in the SMIP1Aa assay. As shown in Table 7 and Table 8, SMIPs have insecticidal activity against Cry-resistant WCR strains indicating that these proteins have a unique mode of action compared to Cry proteins from *Bacillus thuringiensis*. Thus, combinations of SMIPs of the invention, for example SMIP1Aa or SMIP1Aa-W78F/C92L, and Cry proteins would be effective in mitigating the development of resistance to either Cry proteins or SMIPs.

TABLE 7

Insecticidal activity of SMIP1Aa against Cry-Resistant WCR

| SUMO-SMIP1Aa Concentration | Wild-type % Mort. | Wild-type Growth | mCry3A-R % Mort. | mCry3A-R Growth | eCry3.1Ab-R % Mort. | eCry3.1Ab-R Growth |
|---|---|---|---|---|---|---|
| 1X PBS (Neg. Control) | 25 | ml | 0 | ml | 17 | ml |
| 200 µg/mL | 83 | s | 75 | s | 92 | s |
| 100 µg/mL | 50 | sm | 33 | m | 50 | sm |
| 50 µg/mL | 42 | ml | 25 | m | 67 | m |
| 25 µg/mL | 33 | sm | 50 | m | 33 | m |

TABLE 8

Insecticidal activity of SMIP1Aa-W78F/C92L variant against eCry3.1Ab-R WCR.

| SMIP1Aa-W78F/C92L Concentration | Mean % Mortality Day 4 | Mean % Mortality Day 6 |
|---|---|---|
| 200 µg/mL | 100 | 100 |
| 100 µg/mL | 65 | 100 |
| 50 µg/mL | 55 | 100 |

TABLE 8-continued

Insecticidal activity of SMIP1Aa-W78F/C92L
variant against eCry3.1Ab-R WCR.

| SMIP1Aa-W78F/C92L | Mean % Mortality | |
|---|---|---|
| Concentration | Day 4 | Day 6 |
| 25 µg/mL | 25 | 70 |
| 12.5 µg/mL | 35 | 70 |
| 1X PBS | 10 | 15 |

Example 5. Transformation of Maize with SMIP1Aa

A nucleotide sequence that encodes a SMIP1Aa protein or mutant protein, e.g. any of SEQ ID NOs:18-40, or a maize-optimized nucleotide sequence, e.g. any of SEQ ID NOs: 37-40, which can be generated as described in U.S. Pat. No. 6,051,760, is transformed into corn for control of corn rootworm.

Two plant expression cassettes are constructed to introduce the SMIP1Aa-W78F/C92L (SEQ ID NO:39) or the SMIP1Aa-A71L/A90L (SEQ ID NO:38) coding sequence into maize. The first cassette comprises a maize ubiquitin 1 (Ubi1) promoter operably linked to the SMIP1Aa-W78F/C92L or the SMIP1Aa-A71L/A90L coding sequence which is operably linked to a maize Ubi361 terminator. The second cassette comprises a maize Ubi1 promoter operably linked to a pmi coding sequence that encodes the selectable marker phosphomannose isomerase (PMI), which is operably linked to a maize Ubi1 terminator. A recombinant plant transformation binary vector comprising the two expression cassettes is generated for maize transformation experiments.

The binary vector is transformed into *Agrobacterium tumefaciens* using standard molecular biology techniques. To prepare the Agrobacteria for transformation, cells are cultured in liquid YPC media at 28° ° C. and 220 rpm overnight.

*Agrobacterium* transformation of immature maize embryos is performed essentially as described in Negrotto et al., 2000, Plant Cell Reports 19: 798-803. For this example, all media constituents are essentially as described in Negrotto et al., supra. However, various media constituents known in the art may be substituted.

Briefly, *Agrobacterium* strain LBA4404 (pSB1) containing the binary vector plant transformation vector is grown on YEP (yeast extract (5 g/L), peptone (10 g/L), NaCl (5 g/L), 15 g/l agar, pH 6.8) solid medium for 2-4 days at 28° C. Approximately $0.8 \times 10^9$ *Agrobacterium* are suspended in LS-inf media supplemented with 100 µM As (Negrotto et al., supra). Bacteria are pre-induced in this medium for 30-60 minutes.

Immature embryos from a suitable genotype are excised from 8-12 day old ears into liquid LS-inf+100 µM As. Embryos are rinsed once with fresh infection medium. *Agrobacterium* solution is then added and embryos are vortexed for 30 seconds and allowed to settle with the bacteria for 5 minutes. The embryos are then transferred scutellum side up to LSAs medium and cultured in the dark for two to three days. Subsequently, between 20 and 25 embryos per petri plate are transferred to LSDc medium supplemented with cefotaxime (250 mg/l) and silver nitrate (1.6 mg/l) and cultured in the dark for 28° C. for 10 days. Immature embryos, producing embryogenic callus are transferred to LSD1M0.5S medium. The cultures are selected on this medium for about 6 weeks with a subculture step at about 3 weeks. Surviving calli are transferred to Reg1 medium supplemented with mannose. Following culturing in the light (16 hour light/8 hour dark regiment), green tissues are then transferred to Reg2 medium without growth regulators and incubated for about 1-2 weeks. Plantlets are transferred to Magenta GA-7 boxes (Magenta Corp, Chicago Ill.) containing Reg3 medium and grown in the light.

Following transformation, selection, and regeneration, plants are assayed for the presence of the pmi gene and the SMIP1Aa-W78F/C92L (SEQ ID NO:39) or the SMIP1Aa-A71L/A90L (SEQ ID NO:38) maize codon-optimized coding sequence using TaqMan® analysis. Plants were also tested for the presence of the vector backbone. Plants negative for the vector backbone and comprising one copy of the transgene from the binary vector are transferred to the greenhouse and tested for insecticidal activity against WCR.

Example 6. SMIP Toxins in Combination with Second Insecticidal Agent

A SMIP or variant SMIP as described above is purified as in Example 2. Double stranded RNA (dsRNA) complementary to an essential target and known to have insecticidal activity is also prepared. In non-limiting examples, the dsRNA may target a pest insect gene encoding vacuolar ATP synthase, beta-tubulin, 26S proteosome subunit p28 protein, EF1α 48D, troponin I, tetraspanin, clathrin heavy chain, gamma-coatomer, beta-coatomer, and/or juvenile hormone epoxide hydrolase (PCT Patent Application Nos. PCT/US17/044825; PCT/US17/044831; PCT/US17/044832; U.S. Pat. No. 7,812,219; each herein incorporated by reference). The dsRNA and purified protein are tested for efficacy against WCR in a diet-incorporation assay performed essentially as described in Example 1.

Example 7. Genome Editing in Plant Cells In Situ to Generate Modified SMIP Toxins The following Example illustrates the use of genome editing of a plant cell genome in situ to incorporate the mutations described herein (including but not limited to the mutations described in Example 2) into a coding sequence for a native SMIP, including SMIP1Aa (SEQ ID NO: 18), or into a coding sequence for an already modified SMIP1Aa or SMIP2Aa protein.

Targeted genome modification, also known as genome editing, is useful for introducing mutations in specific DNA sequences. These genome editing technologies, which include zinc finger nucleases (ZNFs), transcription activator-like effector nucleases (TALENS), meganucleases and clustered regularly interspaced short palindromic repeats (CRISPR) have been successfully applied to over 50 different organisms including crop plants. See, e.g., Belhaj, K., et al., Plant Methods 9, 39 (2013); Jiang, W., et al., Nucleic Acids Res, 41, e188 (2013)). The CRISPR/Cas system for genome editing is based on transient expression of Cas9 nuclease and an engineered single guide RNA (sgRNA) that specifies the targeted polynucleotide sequence.

Cas9 is a large monomeric DNA nuclease guided to a DNA target sequence with the aid of a complex of two 20-nucleotide (nt) non-coding RNAs: CRIPSR RNA (crRNA) and trans-activating crRNA (tracrRNA), which are functionally available as single synthetic RNA chimera. The Cas9 protein contains two nuclease domains homologous to RuvC and HNH nucleases. The HNH nuclease domain cleaves the complementary DNA strand, whereas the RuvClike domain cleaves the non-complementary strand and, as a result, a blunt cut is introduced in the target DNA.

When the Cas9 and the sgRNA are transiently expressed in living maize cells, double strand breaks (DSBs) in the specific targeted DNA is created in the transgenic maize cell. Mutation at the break site is introduced through the non-homologous end joining and homology-directed DNA repair pathways.

Specific mutations, for example mutations described in Example 2 above, are introduced into a coding sequence for the native SMIP1Aa insecticidal protein (SEQ ID NO: 1) or a mutant SMIP1Aa protein, through the use of recombinant plasmids expressing the Cas9 nuclease and the sgRNA target that is maize codon optimized for the SMIP1Aa or mutant SMIP1Aa sequence in the transgenic maize. Implementation of the method is by an agroinfiltration method with *Agrobacterium tumefaciens* carrying the binary plasmid harboring the specified target sequence of interest. After the sgRNA binds to the target SMIP1Aa or mutant SMIP1Aa coding sequence, the Cas9 nuclease makes specific cuts into the coding sequence and introduces the desired mutation(s) during DNA repair. Thus, a now mutated SMIP1Aa coding sequence will encode an modified SMIP1Aa variant protein, such as the variants described in Example 2, for example, where a mutation at position 71 replaces alanine (A) with leucine (L), or where a mutation at position 90 replaces an alanine (A) with leucine (L), or where a mutation at position 92 replaces a cysteine (C) with leucine (L) or with serine (S), or where a mutation at position 84 replaces glycine (G) with leucine (L), or where a mutation at position 85 replaces a glycine (G) with leucine (L), or where a mutation at position 76 replaces valine (V) with leucine (L), or where a mutation at position 78 replaces a tryptophan (W) with a phenylalanine (F), or any combination thereof.

Plant cells comprising the genome edited SMIP1Aa coding sequences are screened by PCR and sequencing. Calli that harbor genome edited mutations in the SMIP1Aa or modified SMIP1Aa coding sequences are induced to regenerate plants for phenotype evaluation for insecticidal activity of the expressed SMIP1Aa protein against western corn rootworm (*Diabrotica virgifera*), Northern Corn Rootworm (*Diabrotica barberi*), Southern Corn Rootworm (*Diabrotica undecimpunctata howardi*) and/or Mexican Corn Rootworm (*Diabrotica virgifera zeae*).

It should be understood that the examples and embodiments described herein are for illustrative purposes only and that various modifications or changes in light thereof of the description will be suggested to persons skilled in the art and are to be included within the spirit and purview of this application and the scope of the appended claims.

All publications and patent applications mentioned in this specification are indicative of the level of skill of those skilled in the art that this invention pertains. All publications and patent applications are herein incorporated by reference to the same extent as if each individual publication or patent application was specifically and individually indicated to be incorporated by reference.

What is claimed is:

1. A nucleic acid molecule (a) comprising a nucleotide sequence that encodes a mutant, insecticidal protein that comprises the amino acid sequence of any one of SEQ ID NOs: 2-10, 12-14 or (b) comprising the nucleotide sequence of any one of SEQ ID NOs: 21-29 or 31-33.

2. A chimeric gene comprising a heterologous promoter operably linked to the nucleic acid molecule of claim 1.

3. A mutant, insecticidal protein comprising the amino acid sequence of any one of SEQ ID NOs: 2-10, 12-14.

4. A recombinant vector comprising the chimeric gene of claim 2.

5. A host cell comprising the recombinant vector of claim 4, wherein the host cell is a bacterial cell or a maize plant cell.

6. A maize transgenic plant or, part thereof, plant part comprising the transgenic maize plant cell of claim 5.

7. An insecticidal composition comprising the mutant, insecticidal protein of claim 3 and an agriculturally acceptable carrier.

8. A method for producing the mutant, insecticidal protein, comprising culturing the host cell of claim 5 under conditions in which the host cell produces the insecticidal protein.

9. A method of producing a transgenic maize plant, or transgenic maize plant part, having enhanced Western corn rootworm resistance compared to a control maize plant, or control maize plant part, comprising: introducing into a maize plant, or maize plant part, the chimeric gene of claim 2, wherein the encoded mutant, insecticidal protein is expressed in the maize plant, or maize plant part; thereby producing a transgenic maize plant, or transgenic maize plant part, with enhanced Western corn rootworm resistance.

10. The method of claim 9, wherein the introducing step is achieved by (a) transforming the maize plant, or maize plant part, or (b) crossing a first maize plant that comprises the chimeric gene with a different, second maize plant.

11. A method of controlling a Western corn rootworm pest comprising, delivering to the Western corn rootworm pest an effective amount of the mutant, insecticidal protein of claim 3.

12. The method of claim 11, wherein the mutant, insecticidal protein is delivered (a) through a transgenic maize plant, or transgenic maize plant part, or (b) by topical application of an insecticidal composition that comprises the mutant, insecticidal protein.

* * * * *

SEQUENCE LISTING

```
<160> NUMBER OF SEQ ID NOS: 40

<210> SEQ ID NO 1
<211> LENGTH: 118
<212> TYPE: PRT
<213> ORGANISM: Streptomyces species

<400> SEQUENCE: 1

Met Ala Ala Arg Ser Tyr Glu Ile Ala Ile Val Asn Leu Thr Asp Val
1               5                   10                  15

Glu Phe Thr Arg Lys Glu Ala His Leu Asp His Gly Val Trp Ser Lys
            20                  25                  30

Asp Gly Asn Tyr Thr Pro Pro Asp Lys Ile Ser Thr Gly Gln Thr Ala
        35                  40                  45

His Phe Gly Ser Glu Ser Gln Gly Val Ala Thr Gly Thr Glu Gly His
    50                  55                  60

Val Ile Tyr Ser Ser Ser Ala Gly Asp Phe Arg Val Asp Trp Asp Asn
65                  70                  75                  80

Pro Tyr Ile Gly Gly Asp Ser Ser Ser Ala Lys Cys Pro Pro Ser Tyr
                85                  90                  95

Glu Lys Val Leu Ser Asp Ser Lys Gly Asn Asp Ala Thr Leu Lys Val
                100                 105                 110

Val Phe Tyr Lys Lys Ser
            115

<210> SEQ ID NO 2
<211> LENGTH: 118
<212> TYPE: PRT
<213> ORGANISM: Artificial Sequence
<220> FEATURE:
<223> OTHER INFORMATION: SMIP1Aa-A71L
```

-continued

```
<400> SEQUENCE: 2

Met Ala Ala Arg Ser Tyr Glu Ile Ala Ile Val Asn Leu Thr Asp Val
1               5                   10                  15

Glu Phe Thr Arg Lys Glu Ala His Leu Asp His Gly Val Trp Ser Lys
            20                  25                  30

Asp Gly Asn Tyr Thr Pro Pro Asp Lys Ile Ser Thr Gly Gln Thr Ala
        35                  40                  45

His Phe Gly Ser Glu Ser Gln Gly Val Ala Thr Gly Thr Glu Gly His
    50                  55                  60

Val Ile Tyr Ser Ser Ser Leu Gly Asp Phe Arg Val Asp Trp Asp Asn
65                  70                  75                  80

Pro Tyr Ile Gly Gly Asp Ser Ser Ala Lys Cys Pro Pro Ser Tyr
                85                  90                  95

Glu Lys Val Leu Ser Asp Ser Lys Gly Asn Asp Ala Thr Leu Lys Val
            100                 105                 110

Val Phe Tyr Lys Lys Ser
        115

<210> SEQ ID NO 3
<211> LENGTH: 118
<212> TYPE: PRT
<213> ORGANISM: Artificial Sequence
<220> FEATURE:
<223> OTHER INFORMATION: SMIP1Aa-A90L

<400> SEQUENCE: 3

Met Ala Ala Arg Ser Tyr Glu Ile Ala Ile Val Asn Leu Thr Asp Val
1               5                   10                  15

Glu Phe Thr Arg Lys Glu Ala His Leu Asp His Gly Val Trp Ser Lys
            20                  25                  30

Asp Gly Asn Tyr Thr Pro Pro Asp Lys Ile Ser Thr Gly Gln Thr Ala
        35                  40                  45

His Phe Gly Ser Glu Ser Gln Gly Val Ala Thr Gly Thr Glu Gly His
    50                  55                  60

Val Ile Tyr Ser Ser Ser Ala Gly Asp Phe Arg Val Asp Trp Asp Asn
65                  70                  75                  80

Pro Tyr Ile Gly Gly Asp Ser Ser Leu Lys Cys Pro Pro Ser Tyr
                85                  90                  95

Glu Lys Val Leu Ser Asp Ser Lys Gly Asn Asp Ala Thr Leu Lys Val
            100                 105                 110

Val Phe Tyr Lys Lys Ser
        115

<210> SEQ ID NO 4
<211> LENGTH: 118
<212> TYPE: PRT
<213> ORGANISM: Artificial Sequence
<220> FEATURE:
<223> OTHER INFORMATION: SMIP1Aa-C92L

<400> SEQUENCE: 4

Met Ala Ala Arg Ser Tyr Glu Ile Ala Ile Val Asn Leu Thr Asp Val
1               5                   10                  15

Glu Phe Thr Arg Lys Glu Ala His Leu Asp His Gly Val Trp Ser Lys
            20                  25                  30

Asp Gly Asn Tyr Thr Pro Pro Asp Lys Ile Ser Thr Gly Gln Thr Ala
        35                  40                  45
```

His Phe Gly Ser Glu Ser Gln Gly Val Ala Thr Gly Thr Glu Gly His
    50                  55                  60

Val Ile Tyr Ser Ser Ser Ala Gly Asp Phe Arg Val Asp Trp Asp Asn
 65                  70                  75                  80

Pro Tyr Ile Gly Gly Asp Ser Ser Ala Lys Leu Pro Pro Ser Tyr
                85                  90                  95

Glu Lys Val Leu Ser Asp Ser Lys Gly Asn Asp Ala Thr Leu Lys Val
                100                 105                 110

Val Phe Tyr Lys Lys Ser
            115

<210> SEQ ID NO 5
<211> LENGTH: 118
<212> TYPE: PRT
<213> ORGANISM: Artificial Sequence
<220> FEATURE:
<223> OTHER INFORMATION: SMIP1Aa-C92S

<400> SEQUENCE: 5

Met Ala Ala Arg Ser Tyr Glu Ile Ala Ile Val Asn Leu Thr Asp Val
  1               5                  10                  15

Glu Phe Thr Arg Lys Glu Ala His Leu Asp His Gly Val Trp Ser Lys
                20                  25                  30

Asp Gly Asn Tyr Thr Pro Pro Asp Lys Ile Ser Thr Gly Gln Thr Ala
            35                  40                  45

His Phe Gly Ser Glu Ser Gln Gly Val Ala Thr Gly Thr Glu Gly His
    50                  55                  60

Val Ile Tyr Ser Ser Ser Ala Gly Asp Phe Arg Val Asp Trp Asp Asn
 65                  70                  75                  80

Pro Tyr Ile Gly Gly Asp Ser Ser Ser Ala Lys Ser Pro Pro Ser Tyr
                85                  90                  95

Glu Lys Val Leu Ser Asp Ser Lys Gly Asn Asp Ala Thr Leu Lys Val
                100                 105                 110

Val Phe Tyr Lys Lys Ser
            115

<210> SEQ ID NO 6
<211> LENGTH: 118
<212> TYPE: PRT
<213> ORGANISM: Artificial Sequence
<220> FEATURE:
<223> OTHER INFORMATION: SMIP1Aa-G84L

<400> SEQUENCE: 6

Met Ala Ala Arg Ser Tyr Glu Ile Ala Ile Val Asn Leu Thr Asp Val
  1               5                  10                  15

Glu Phe Thr Arg Lys Glu Ala His Leu Asp His Gly Val Trp Ser Lys
                20                  25                  30

Asp Gly Asn Tyr Thr Pro Pro Asp Lys Ile Ser Thr Gly Gln Thr Ala
            35                  40                  45

His Phe Gly Ser Glu Ser Gln Gly Val Ala Thr Gly Thr Glu Gly His
    50                  55                  60

Val Ile Tyr Ser Ser Ser Ala Gly Asp Phe Arg Val Asp Trp Asp Asn
 65                  70                  75                  80

Pro Tyr Ile Leu Gly Asp Ser Ser Ser Ala Lys Cys Pro Pro Ser Tyr
                85                  90                  95

Glu Lys Val Leu Ser Asp Ser Lys Gly Asn Asp Ala Thr Leu Lys Val
                100                 105                 110

Val Phe Tyr Lys Lys Ser
        115

<210> SEQ ID NO 7
<211> LENGTH: 118
<212> TYPE: PRT
<213> ORGANISM: Artificial Sequence
<220> FEATURE:
<223> OTHER INFORMATION: SMIP1Aa-G85L

<400> SEQUENCE: 7

Met Ala Ala Arg Ser Tyr Glu Ile Ala Ile Val Asn Leu Thr Asp Val
1               5                   10                  15

Glu Phe Thr Arg Lys Glu Ala His Leu Asp His Gly Val Trp Ser Lys
            20                  25                  30

Asp Gly Asn Tyr Thr Pro Pro Asp Lys Ile Ser Thr Gly Gln Thr Ala
        35                  40                  45

His Phe Gly Ser Glu Ser Gln Gly Val Ala Thr Gly Thr Glu Gly His
    50                  55                  60

Val Ile Tyr Ser Ser Ser Ala Gly Asp Phe Arg Val Asp Trp Asp Asn
65                  70                  75                  80

Pro Tyr Ile Gly Leu Asp Ser Ser Ala Lys Cys Pro Pro Ser Tyr
                85                  90                  95

Glu Lys Val Leu Ser Asp Ser Lys Gly Asn Asp Ala Thr Leu Lys Val
            100                 105                 110

Val Phe Tyr Lys Lys Ser
        115

<210> SEQ ID NO 8
<211> LENGTH: 118
<212> TYPE: PRT
<213> ORGANISM: Artificial Sequence
<220> FEATURE:
<223> OTHER INFORMATION: SMIP1Aa-V76L

<400> SEQUENCE: 8

Met Ala Ala Arg Ser Tyr Glu Ile Ala Ile Val Asn Leu Thr Asp Val
1               5                   10                  15

Glu Phe Thr Arg Lys Glu Ala His Leu Asp His Gly Val Trp Ser Lys
            20                  25                  30

Asp Gly Asn Tyr Thr Pro Pro Asp Lys Ile Ser Thr Gly Gln Thr Ala
        35                  40                  45

His Phe Gly Ser Glu Ser Gln Gly Val Ala Thr Gly Thr Glu Gly His
    50                  55                  60

Val Ile Tyr Ser Ser Ser Ala Gly Asp Phe Arg Leu Asp Trp Asp Asn
65                  70                  75                  80

Pro Tyr Ile Gly Gly Asp Ser Ser Ala Lys Cys Pro Pro Ser Tyr
                85                  90                  95

Glu Lys Val Leu Ser Asp Ser Lys Gly Asn Asp Ala Thr Leu Lys Val
            100                 105                 110

Val Phe Tyr Lys Lys Ser
        115

<210> SEQ ID NO 9
<211> LENGTH: 118
<212> TYPE: PRT
<213> ORGANISM: Artificial Sequence
<220> FEATURE:
<223> OTHER INFORMATION: SMIP1Aa-W78F

<400> SEQUENCE: 9

```
Met Ala Arg Ser Tyr Glu Ile Ala Ile Val Asn Leu Thr Asp Val
1               5                   10                  15

Glu Phe Thr Arg Lys Glu Ala His Leu Asp His Gly Val Trp Ser Lys
            20                  25                  30

Asp Gly Asn Tyr Thr Pro Pro Asp Lys Ile Ser Thr Gly Gln Thr Ala
        35                  40                  45

His Phe Gly Ser Glu Ser Gln Gly Val Ala Thr Gly Thr Glu Gly His
    50                  55                  60

Val Ile Tyr Ser Ser Ser Ala Gly Asp Phe Arg Val Asp Phe Asp Asn
65                  70                  75                  80

Pro Tyr Ile Gly Gly Asp Ser Ser Ser Ala Lys Cys Pro Pro Ser Tyr
                85                  90                  95

Glu Lys Val Leu Ser Asp Ser Lys Gly Asn Asp Ala Thr Leu Lys Val
            100                 105                 110

Val Phe Tyr Lys Lys Ser
            115
```

<210> SEQ ID NO 10
<211> LENGTH: 118
<212> TYPE: PRT
<213> ORGANISM: Artificial Sequence
<220> FEATURE:
<223> OTHER INFORMATION: SMIP1Aa-A71L/A90L

<400> SEQUENCE: 10

```
Met Ala Ala Arg Ser Tyr Glu Ile Ala Ile Val Asn Leu Thr Asp Val
1               5                   10                  15

Glu Phe Thr Arg Lys Glu Ala His Leu Asp His Gly Val Trp Ser Lys
            20                  25                  30

Asp Gly Asn Tyr Thr Pro Pro Asp Lys Ile Ser Thr Gly Gln Thr Ala
        35                  40                  45

His Phe Gly Ser Glu Ser Gln Gly Val Ala Thr Gly Thr Glu Gly His
    50                  55                  60

Val Ile Tyr Ser Ser Ser Leu Gly Asp Phe Arg Val Asp Trp Asp Asn
65                  70                  75                  80

Pro Tyr Ile Gly Gly Asp Ser Ser Ser Leu Lys Cys Pro Pro Ser Tyr
                85                  90                  95

Glu Lys Val Leu Ser Asp Ser Lys Gly Asn Asp Ala Thr Leu Lys Val
            100                 105                 110

Val Phe Tyr Lys Lys Ser
            115
```

<210> SEQ ID NO 11
<211> LENGTH: 118
<212> TYPE: PRT
<213> ORGANISM: Artificial Sequence
<220> FEATURE:
<223> OTHER INFORMATION: SMIP1Aa-A71L/W78F

<400> SEQUENCE: 11

```
Met Ala Ala Arg Ser Tyr Glu Ile Ala Ile Val Asn Leu Thr Asp Val
1               5                   10                  15

Glu Phe Thr Arg Lys Glu Ala His Leu Asp His Gly Val Trp Ser Lys
            20                  25                  30

Asp Gly Asn Tyr Thr Pro Pro Asp Lys Ile Ser Thr Gly Gln Thr Ala
        35                  40                  45
```

His Phe Gly Ser Glu Ser Gln Gly Val Ala Thr Gly Thr Glu Gly His
        50                  55                  60

Val Ile Tyr Ser Ser Ser Leu Gly Asp Phe Arg Val Asp Phe Asp Asn
 65                  70                  75                  80

Pro Tyr Ile Gly Gly Asp Ser Ser Ala Lys Cys Pro Pro Ser Tyr
                85                  90                  95

Glu Lys Val Leu Ser Asp Ser Lys Gly Asn Asp Ala Thr Leu Lys Val
                100                 105                 110

Val Phe Tyr Lys Lys Ser
            115

<210> SEQ ID NO 12
<211> LENGTH: 118
<212> TYPE: PRT
<213> ORGANISM: Artificial Sequence
<220> FEATURE:
<223> OTHER INFORMATION: SMIP1Aa-W78F/C92L

<400> SEQUENCE: 12

Met Ala Ala Arg Ser Tyr Glu Ile Ala Ile Val Asn Leu Thr Asp Val
 1               5                  10                  15

Glu Phe Thr Arg Lys Glu Ala His Leu Asp His Gly Val Trp Ser Lys
                20                  25                  30

Asp Gly Asn Tyr Thr Pro Pro Asp Lys Ile Ser Thr Gly Gln Thr Ala
                35                  40                  45

His Phe Gly Ser Glu Ser Gln Gly Val Ala Thr Gly Thr Glu Gly His
        50                  55                  60

Val Ile Tyr Ser Ser Ser Ala Gly Asp Phe Arg Val Asp Phe Asp Asn
 65                  70                  75                  80

Pro Tyr Ile Gly Gly Asp Ser Ser Ala Lys Leu Pro Pro Ser Tyr
                85                  90                  95

Glu Lys Val Leu Ser Asp Ser Lys Gly Asn Asp Ala Thr Leu Lys Val
                100                 105                 110

Val Phe Tyr Lys Lys Ser
            115

<210> SEQ ID NO 13
<211> LENGTH: 118
<212> TYPE: PRT
<213> ORGANISM: Artificial Sequence
<220> FEATURE:
<223> OTHER INFORMATION: SMIP1Aa-Y82F/I83L

<400> SEQUENCE: 13

Met Ala Ala Arg Ser Tyr Glu Ile Ala Ile Val Asn Leu Thr Asp Val
 1               5                  10                  15

Glu Phe Thr Arg Lys Glu Ala His Leu Asp His Gly Val Trp Ser Lys
                20                  25                  30

Asp Gly Asn Tyr Thr Pro Pro Asp Lys Ile Ser Thr Gly Gln Thr Ala
                35                  40                  45

His Phe Gly Ser Glu Ser Gln Gly Val Ala Thr Gly Thr Glu Gly His
        50                  55                  60

Val Ile Tyr Ser Ser Ala Gly Asp Phe Arg Val Asp Trp Asp Asn
 65                  70                  75                  80

Pro Phe Leu Gly Gly Asp Ser Ser Ala Lys Cys Pro Pro Ser Tyr
                85                  90                  95

Glu Lys Val Leu Ser Asp Ser Lys Gly Asn Asp Ala Thr Leu Lys Val

```
              100                 105                 110

Val Phe Tyr Lys Lys Ser
        115

<210> SEQ ID NO 14
<211> LENGTH: 118
<212> TYPE: PRT
<213> ORGANISM: Artificial Sequence
<220> FEATURE:
<223> OTHER INFORMATION: SMIP1Aa-A2G/A3G

<400> SEQUENCE: 14

Met Gly Gly Arg Ser Tyr Glu Ile Ala Ile Val Asn Leu Thr Asp Val
1               5                   10                  15

Glu Phe Thr Arg Lys Glu Ala His Leu Asp His Gly Val Trp Ser Lys
            20                  25                  30

Asp Gly Asn Tyr Thr Pro Pro Asp Lys Ile Ser Thr Gly Gln Thr Ala
        35                  40                  45

His Phe Gly Ser Glu Ser Gln Gly Val Ala Thr Gly Thr Glu Gly His
    50                  55                  60

Val Ile Tyr Ser Ser Ser Ala Gly Asp Phe Arg Val Asp Trp Asp Asn
65                  70                  75                  80

Pro Tyr Ile Gly Gly Asp Ser Ser Ala Lys Cys Pro Pro Ser Tyr
                85                  90                  95

Glu Lys Val Leu Ser Asp Ser Lys Gly Asn Asp Ala Thr Leu Lys Val
                100                 105                 110

Val Phe Tyr Lys Lys Ser
        115

<210> SEQ ID NO 15
<211> LENGTH: 118
<212> TYPE: PRT
<213> ORGANISM: Artificial Sequence
<220> FEATURE:
<223> OTHER INFORMATION: SMIP1Aa-A2V/A3V

<400> SEQUENCE: 15

Met Val Val Arg Ser Tyr Glu Ile Ala Ile Val Asn Leu Thr Asp Val
1               5                   10                  15

Glu Phe Thr Arg Lys Glu Ala His Leu Asp His Gly Val Trp Ser Lys
            20                  25                  30

Asp Gly Asn Tyr Thr Pro Pro Asp Lys Ile Ser Thr Gly Gln Thr Ala
        35                  40                  45

His Phe Gly Ser Glu Ser Gln Gly Val Ala Thr Gly Thr Glu Gly His
    50                  55                  60

Val Ile Tyr Ser Ser Ser Ala Gly Asp Phe Arg Val Asp Trp Asp Asn
65                  70                  75                  80

Pro Tyr Ile Gly Gly Asp Ser Ser Ala Lys Cys Pro Pro Ser Tyr
                85                  90                  95

Glu Lys Val Leu Ser Asp Ser Lys Gly Asn Asp Ala Thr Leu Lys Val
                100                 105                 110

Val Phe Tyr Lys Lys Ser
        115

<210> SEQ ID NO 16
<211> LENGTH: 237
<212> TYPE: PRT
<213> ORGANISM: Artificial Sequence
<220> FEATURE:
```

<223> OTHER INFORMATION: SUMO-SMIP1Aa

<400> SEQUENCE: 16

```
Met Gly Ser Ser His His His His His His Gly Ser Gly Leu Val Pro
1               5                   10                  15

Arg Gly Ser Ala Ser Met Ser Asp Ser Glu Val Asn Gln Glu Ala Lys
            20                  25                  30

Pro Glu Val Lys Pro Glu Val Lys Pro Glu Thr His Ile Asn Leu Lys
        35                  40                  45

Val Ser Asp Gly Ser Ser Glu Ile Phe Phe Lys Ile Lys Lys Thr Thr
    50                  55                  60

Pro Leu Arg Arg Leu Met Glu Ala Phe Ala Lys Arg Gln Gly Lys Glu
65                  70                  75                  80

Met Asp Ser Leu Arg Phe Leu Tyr Asp Gly Ile Arg Ile Gln Ala Asp
                85                  90                  95

Gln Thr Pro Glu Asp Leu Asp Met Glu Asp Asn Asp Ile Ile Glu Ala
            100                 105                 110

His Arg Glu Gln Ile Gly Gly Met Ala Ala Arg Ser Tyr Glu Ile Ala
        115                 120                 125

Ile Val Asn Leu Thr Asp Val Glu Phe Thr Arg Lys Glu Ala His Leu
    130                 135                 140

Asp His Gly Val Trp Ser Lys Asp Gly Asn Tyr Thr Pro Pro Asp Lys
145                 150                 155                 160

Ile Ser Thr Gly Gln Thr Ala His Phe Gly Ser Glu Ser Gln Gly Val
                165                 170                 175

Ala Thr Gly Thr Glu Gly His Val Ile Tyr Ser Ser Ala Gly Asp
            180                 185                 190

Phe Arg Val Asp Trp Asp Asn Pro Tyr Ile Gly Gly Asp Ser Ser Ser
        195                 200                 205

Ala Lys Cys Pro Pro Ser Tyr Glu Lys Val Leu Ser Asp Ser Lys Gly
    210                 215                 220

Asn Asp Ala Thr Leu Lys Val Val Phe Tyr Lys Lys Ser
225                 230                 235
```

<210> SEQ ID NO 17
<211> LENGTH: 150
<212> TYPE: PRT
<213> ORGANISM: Streptomyces species

<400> SEQUENCE: 17

```
Met Ser Glu Asn Val Thr Gly Ala His Pro Tyr Gly Ser Ile His Trp
1               5                   10                  15

Val Pro Glu Ile Phe Val Asp Pro Ala Lys Ser Arg Gly Glu Gln Asp
            20                  25                  30

Met Ala Ala Arg Ser Tyr Asp Ile Ser Ile Val Asn Leu Thr Asn Met
        35                  40                  45

Glu Leu Thr Arg Glu Lys Ser His Leu Asp His Gly Val Trp Ser Gly
    50                  55                  60

Glu Gly Ser Glu Thr Pro Pro Asp Lys Ile Ala Pro Gly Glu Thr Val
65                  70                  75                  80

His Phe Gly Ser Glu Ser Gln Gly Phe Met Thr Gly Thr Glu Gly Tyr
                85                  90                  95

Val Thr Tyr Gly Ser Pro Ala Gly Asp Phe Thr Val Tyr Trp Asp Asn
            100                 105                 110

Pro Tyr Val Gly Ser Asp Ser Ser Ser Ala Thr Cys Pro Ser Gly Tyr
```

```
                    115                 120                 125
        Glu Lys Val Lys Ser Asp Ser Ala Gly Asn Asn Ala Thr Leu Lys Val
            130                 135                 140

Val Phe Tyr Glu Asn Ser
        145                 150
```

<210> SEQ ID NO 18
<211> LENGTH: 357
<212> TYPE: DNA
<213> ORGANISM: Streptomyces species

<400> SEQUENCE: 18

```
atggccgcaa ggtcgtacga aatcgcgatc gtcaacctta ccgacgtgga gttcacgcgc    60
aaagaggcac atctcgatca tggggtgtgg agcaaggacg ggaactacac gcctccggac   120
aagatcagca ccggtcagac agcgcatttc ggaagtgaat cccagggagt ggcgaccgga   180
accgaggggc atgtgatcta ttcgtccagc gccggggatt ttcgcgtcga ctgggacaac   240
ccctacatcg ggggtgactc atcctccgcg aagtgcccgc cctcttacga aaaggtgctc   300
agtgactcca aggtaacga cgcaaccctg aaggtggtct tctacaagaa gagctga       357
```

<210> SEQ ID NO 19
<211> LENGTH: 453
<212> TYPE: DNA
<213> ORGANISM: Streptomyces species

<400> SEQUENCE: 19

```
atgtctgaaa acgtgactgg tgcccatcca tatgggtcta tacattgggt cccggaaatc    60
ttcgtagatc cggcgaaaag ccgaggggag caggacatgg ccgcgagatc ctacgatatc   120
tcgatcgtca acctcaccaa tatggaactg acccgggaga gtcgcacct ggaccacggg    180 gtgtggagcg gggaaggcag cgaaacaccc ccggacaaga tagccccgg agaaacggtg    240 catttcggca gcgaatccca gggattcatg acgggaaccg aagggtacgt cacctacggc   300
tcgcccgccg agacttcac cgtctactgg gacaacccgt atgtcggttc ggattcgtcg    360
tccgcgacgt gcccgtcggg ttacgaaaag gtcaagagcg actccgcggg caacaacgcg   420
accctgaagg tggtcttcta cgagaacagc tga                                453
```

<210> SEQ ID NO 20
<211> LENGTH: 357
<212> TYPE: DNA
<213> ORGANISM: Artificial Sequence
<220> FEATURE:
<223> OTHER INFORMATION: E. coli optimized SMIP1Aa.

<400> SEQUENCE: 20

```
atggccgccc gtagttatga aattgcaatt gttaacttaa cggatgtaga atttacccgg    60
aaagaagccc atctcgacca cggagtttgg agcaaggatg gtaattacac tccgccggat   120
aaaatctcca ccgggcagac ggctcatttt ggtagcgaga gtcagggagt tgctaccggt   180
accgaaggtc atgtaattta ctcctccagc gcggggggact ccgcgtcga ttgggataat    240 ccatacattg gtggcgactc tagcagcgct aaatgccac cgtcgtacga aaaagttctg     300
tccgattcca agggtaacga tgcaaccta aaagtggtct tttataaaaa gtcctaa       357
```

<210> SEQ ID NO 21
<211> LENGTH: 357
<212> TYPE: DNA
<213> ORGANISM: Artificial Sequence -continued

```
<220> FEATURE:
<223> OTHER INFORMATION: E. coli optimized SMIP1Aa-A71L.

<400> SEQUENCE: 21
atggccgccc gtagttatga aattgcaatt gttaacttaa cggatgtaga atttacccgg 60
aaagaagccc atctcgacca cggagtttgg agcaaggatg gtaattacac tccgccggat 120
aaaatctcca ccgggcagac ggctcatttt ggtagcgaga gtcagggagt tgctaccggt 180
accgaaggtc atgtaattta ctcctccagc ttaggggact tccgcgtcga ttgggataat 240
ccatacattg gtggcgactc tagcagcgct aaatgcccac cgtcgtacga aaaagttctg 300
tccgattcca agggtaacga tgcaacctta aaagtggtct tttataaaaa gtcctaa 357

<210> SEQ ID NO 22
<211> LENGTH: 357
<212> TYPE: DNA
<213> ORGANISM: Artificial Sequence
<220> FEATURE:
<223> OTHER INFORMATION: E. coli optimized SMIP1Aa-A90L.

<400> SEQUENCE: 22
atggccgccc gtagttatga aattgcaatt gttaacttaa cggatgtaga atttacccgg 60
aaagaagccc atctcgacca cggagtttgg agcaaggatg gtaattacac tccgccggat 120
aaaatctcca ccgggcagac ggctcatttt ggtagcgaga gtcagggagt tgctaccggt 180
accgaaggtc atgtaattta ctcctccagc gcgggggact tccgcgtcga ttgggataat 240
ccatacattg gtggcgactc tagcagctta aaatgcccac cgtcgtacga aaaagttctg 300
tccgattcca agggtaacga tgcaacctta aaagtggtct tttataaaaa gtcctaa 357

<210> SEQ ID NO 23
<211> LENGTH: 357
<212> TYPE: DNA
<213> ORGANISM: Artificial Sequence
<220> FEATURE:
<223> OTHER INFORMATION: E. coli optimized SMIP1Aa-C92L.

<400> SEQUENCE: 23
atggccgccc gtagttatga aattgcaatt gttaacttaa cggatgtaga atttacccgg 60
aaagaagccc atctcgacca cggagtttgg agcaaggatg gtaattacac tccgccggat 120
aaaatctcca ccgggcagac ggctcatttt ggtagcgaga gtcagggagt tgctaccggt 180
accgaaggtc atgtaattta ctcctccagc gcgggggact tccgcgtcga ttgggataat 240
ccatacattg gtggcgactc tagcagcgct aaactgccac cgtcgtacga aaaagttctg 300
tccgattcca agggtaacga tgcaacctta aaagtggtct tttataaaaa gtcctaa 357

<210> SEQ ID NO 24
<211> LENGTH: 357
<212> TYPE: DNA
<213> ORGANISM: Artificial Sequence
<220> FEATURE:
<223> OTHER INFORMATION: E. coli optimized SMIP1Aa-C92C.

<400> SEQUENCE: 24
atggccgccc gtagttatga aattgcaatt gttaacttaa cggatgtaga atttacccgg 60
aaagaagccc atctcgacca cggagtttgg agcaaggatg gtaattacac tccgccggat 120
aaaatctcca ccgggcagac ggctcatttt ggtagcgaga gtcagggagt tgctaccggt 180
accgaaggtc atgtaattta ctcctccagc gcgggggact tccgcgtcga ttgggataat 240
```

```
ccatacattg gtggcgactc tagcagcgct aaatccccac cgtcgtacga aaaagttctg    300
tccgattcca agggtaacga tgcaaccttc aaagtggtct tttataaaaa gtcctaa      357
```

<210> SEQ ID NO 25
<211> LENGTH: 357
<212> TYPE: DNA
<213> ORGANISM: Artificial Sequence
<220> FEATURE:
<223> OTHER INFORMATION: E. coli optimized SMIP1Aa-G84L.

<400> SEQUENCE: 25

```
atggccgccc gtagttatga aattgcaatt gttaacttaa cggatgtaga atttacccgg    60
aaagaagccc atctcgacca cggagtttgg agcaaggatg gtaattacac tccgccggat    120
aaaatctcca ccgggcagac ggctcatttt ggtagcgaga gtcagggagt tgctaccggt    180
accgaaggtc atgtaattta ctcctccagc gcggggact tccgcgtcga ttgggataat     240
ccatacattt taggcgactc tagcagcgct aaatgcccac cgtcgtacga aaaagttctg    300
tccgattcca agggtaacga tgcaaccttc aaagtggtct tttataaaaa gtcctaa      357
```

<210> SEQ ID NO 26
<211> LENGTH: 357
<212> TYPE: DNA
<213> ORGANISM: Artificial Sequene
<220> FEATURE:
<223> OTHER INFORMATION: E. coli opti mized SMIP1Aa-G85L.

<400> SEQUENCE: 26

```
atggccgccc gtagttatga aattgcaatt gttaacttaa cggatgtaga atttacccgg    60
aaagaagccc atctcgacca cggagtttgg agcaaggatg gtaattacac tccgccggat    120
aaaatctcca ccgggcagac ggctcatttt ggtagcgaga gtcagggagt tgctaccggt    180
accgaaggtc atgtaattta ctcctccagc gcggggact tccgcgtcga ttgggataat     240
ccatacattg ttttagactc tagcagcgct aaatgcccac cgtcgtacga aaaagttctg    300
tccgattcca agggtaacga tgcaaccttc aaagtggtct tttataaaaa gtcctaa      357
```

<210> SEQ ID NO 27
<211> LENGTH: 357
<212> TYPE: DNA
<213> ORGANISM: Artificial Sequence
<220> FEATURE:
<223> OTHER INFORMATION: E. coli optimized SMIP1Aa-V76L.

<400> SEQUENCE: 27

```
atggccgccc gtagttatga aattgcaatt gttaacttaa cggatgtaga atttacccgg    60
aaagaagccc atctcgacca cggagtttgg agcaaggatg gtaattacac tccgccggat    120
aaaatctcca ccgggcagac ggctcatttt ggtagcgaga gtcagggagt tgctaccggt    180
accgaaggtc atgtaattta ctcctccagc gcggggact tccgcttaga ttgggataat     240
ccatacattg gtggcgactc tagcagcgct aaatgcccac cgtcgtacga aaaagttctg    300
tccgattcca agggtaacga tgcaaccttc aaagtggtct tttataaaaa gtcctaa      357
```

<210> SEQ ID NO 28
<211> LENGTH: 357
<212> TYPE: DNA
<213> ORGANISM: Artificial Sequence
<220> FEATURE:
<223> OTHER INFORMATION: E. coli optimized SMIP1Aa-W78F.

<400> SEQUENCE: 28

```
atggccgccc gtagttatga aattgcaatt gttaacttaa cggatgtaga atttacccgg      60
aaagaagccc atctcgacca cggagtttgg agcaaggatg gtaattacac tccgccggat     120
aaaatctcca ccgggcagac ggctcatttt ggtagcgaga gtcagggagt tgctaccggt     180
accgaaggtc atgtaattta ctcctccagc gcggggact tccgcgtcga ttttgataat     240
ccatacattg gtggcgactc tagcagcgct aaatgcccac cgtcgtacga aaaagttctg     300
tccgattcca agggtaacga tgcaacctta aaagtggtct tttataaaaa gtcctaa      357
```

<210> SEQ ID NO 29
<211> LENGTH: 357
<212> TYPE: DNA
<213> ORGANISM: Artificial Sequence
<220> FEATURE:
<223> OTHER INFORMATION: E. coli optimized SMIP1Aa-A71L/A90L.

<400> SEQUENCE: 29

```
atggccgccc gtagttatga aattgcaatt gttaacttaa cggatgtaga atttacccgg      60
aaagaagccc atctcgacca cggagtttgg agcaaggatg gtaattacac tccgccggat     120
aaaatctcca ccgggcagac ggctcatttt ggtagcgaga gtcagggagt tgctaccggt     180
accgaaggtc atgtaattta ctcctccagc ttaggggact tccgcgtcga ttgggataat     240
ccatacattg gtggcgactc tagcagctta aaatgcccac cgtcgtacga aaaagttctg     300
tccgattcca agggtaacga tgcaacctta aaagtggtct tttataaaaa gtcctaa      357
```

<210> SEQ ID NO 30
<211> LENGTH: 357
<212> TYPE: DNA
<213> ORGANISM: Artificial Sequence
<220> FEATURE:
<223> OTHER INFORMATION: E. coli optimized SMIP1Aa-A71L/W78F.

<400> SEQUENCE: 30

```
atggccgccc gtagttatga aattgcaatt gttaacttaa cggatgtaga atttacccgg      60
aaagaagccc atctcgacca cggagtttgg agcaaggatg gtaattacac tccgccggat     120
aaaatctcca ccgggcagac ggctcatttt ggtagcgaga gtcagggagt tgctaccggt     180
accgaaggtc atgtaattta ctcctccagc ttaggggact tccgcgtcga ttttgataat     240
ccatacattg gtggcgactc tagcagcgct aaatgcccac cgtcgtacga aaaagttctg     300
tccgattcca agggtaacga tgcaacctta aaagtggtct tttataaaaa gtcctaa      357
```

<210> SEQ ID NO 31
<211> LENGTH: 357
<212> TYPE: DNA
<213> ORGANISM: Artificial Sequence
<220> FEATURE:
<223> OTHER INFORMATION: E. coli optimized SMIP1Aa-W78F/C92L.

<400> SEQUENCE: 31

```
atggccgccc gtagttatga aattgcaatt gttaacttaa cggatgtaga atttacccgg     60
aaagaagccc atctcgacca cggagtttgg agcaaggatg gtaattacac tccgccggat    120
aaaatctcca ccgggcagac ggctcatttt ggtagcgaga gtcagggagt tgctaccggt    180
accgaaggtc atgtaattta ctcctccagc gcgggggact tccgcgtcga ttttgataat    240
ccatacattg gtggcgactc tagcagcgct aaactgccac cgtcgtacga aaaagttctg    300
tccgattcca agggtaacga tgcaacctta aaagtggtct tttataaaaa gtcctaa       357
```

<210> SEQ ID NO 32
<211> LENGTH: 357
<212> TYPE: DNA
<213> ORGANISM: Artificial Sequence
<220> FEATURE:
<223> OTHER INFORMATION: E. coli optimized SMIP1Aa-Y82F/I83L.

<400> SEQUENCE: 32

```
atggccgccc gtagttatga aattgcaatt gttaacttaa cggatgtaga atttacccgg    60
aaagaagccc atctcgacca cggagtttgg agcaaggatg gtaattacac tccgccggat   120
aaaatctcca ccgggcagac ggctcatttt ggtagcgaga gtcagggagt tgctaccggt   180
accgaaggtc atgtaattta ctcctccagc gcggggact tccgcgtcga ttgggataat    240
ccattcctgg gtggcgactc tagcagcgct aaatgcccac cgtcgtacga aaaagttctg   300
tccgattcca agggtaacga tgcaacctta aaagtggtct tttataaaaa gtcctaa      357
```

<210> SEQ ID NO 33
<211> LENGTH: 357
<212> TYPE: DNA
<213> ORGANISM: artificial Sequence
<220> FEATURE:
<223> OTHER INFORMATION: E. coli optimized SMIP1Aa-A2G/A3G.

<400> SEQUENCE: 33

```
atgggcggtc gtagttatga aattgcaatt gttaacttaa cggatgtaga atttacccgg    60
aaagaagccc atctcgacca cggagtttgg agcaaggatg gtaattacac tccgccggat   120
aaaatctcca ccgggcagac ggctcatttt ggtagcgaga gtcagggagt tgctaccggt   180
accgaaggtc atgtaattta ctcctccagc gcggggact tccgcgtcga ttgggataat    240
ccatacattg gtggcgactc tagcagcgct aaatgcccac cgtcgtacga aaaagttctg   300
tccgattcca agggtaacga tgcaacctta aaagtggtct tttataaaaa gtcctaa      357
```

<210> SEQ ID NO 34
<211> LENGTH: 357
<212> TYPE: DNA
<213> ORGANISM: Artificial Sequence
<220> FEATURE:
<223> OTHER INFORMATION: E. coli optimized SMIP1Aa-A2V/A3V.

<400> SEQUENCE: 34

```
atggtggtcc gtagttatga aattgcaatt gttaacttaa cggatgtaga atttacccgg    60
aaagaagccc atctcgacca cggagtttgg agcaaggatg gtaattacac tccgccggat   120
aaaatctcca ccgggcagac ggctcatttt ggtagcgaga gtcagggagt tgctaccggt   180
accgaaggtc atgtaattta ctcctccagc gcggggact tccgcgtcga ttgggataat    240
ccatacattg gtggcgactc tagcagcgct aaatgcccac cgtcgtacga aaaagttctg   300
tccgattcca agggtaacga tgcaacctta aaagtggtct tttataaaaa gtcctaa      357
```

<210> SEQ ID NO 35
<211> LENGTH: 714
<212> TYPE: DNA
<213> ORGANISM: Artificial Sequence
<220> FEATURE:
<223> OTHER INFORMATION: E. coli optimized SUMO-SMIP1Aa.

<400> SEQUENCE: 35

```
atgggcagca gccatcatca tcatcatcac ggcagcggcc tggtgccgcg cggcagcgct    60
agcatgtcgg actcagaagt caatcaagaa gctaagccag aggtcaagcc agaagtcaag   120
```

```
cctgagactc acatcaattt aaaggtgtcc gatggatctt cagagatctt cttcaagatc      180
aaaaagacca ctcctttaag aaggctgatg gaagcgttcg ctaaaagaca gggtaaggaa      240
atggactcct taagattctt gtacgacggt attagaattc aagctgatca gaccccctgaa     300 gatttggaca tggaggataa cgatattatt gaggctcaca gagaacagat tggtggtatg      360
gccgcccgta gttatgaaat tgcaattgtt aacttaacgg atgtagaatt tacccggaaa     420
gaagcccatc tcgaccacgg agtttggagc aaggatggta attacactcc gccggataaa     480
atctccaccg ggcagacggc tcattttggt agcgagagtc agggagttgc taccggtacc     540
gaaggtcatg taatttactc ctccagcgcg ggggacttcc gcgtcgattg ggataatcca     600
tacattggtg gcgactctag cagcgctaaa tgcccaccgt cgtacgaaaa agttctgtcc     660
gattccaagg gtaacgatgc aaccttaaaa gtggtctttt ataaaaagtc ctaa           714
```

<210> SEQ ID NO 36
<211> LENGTH: 453
<212> TYPE: DNA
<213> ORGANISM: Artificial Sequence
<220> FEATURE:
<223> OTHER INFORMATION: E. coli optimized SMIP2Aa.

<400> SEQUENCE: 36

```
atgtctgaga atgtgacggg ggcgcatccc tatggctcta tccactgggt ccccgaaatt      60
tttgtagatc cagcgaagtc ccgtggtgag caggacatgg ctgcgcgtag ttacgatatt     120
tcgattgtta atctgactaa catggagctt acccgtgaga aaagtcactt agatcatggc     180
gtctggtctg gagagggaag tgaaacacct cccgacaaga tcgctcccgg tgagactgtc     240
cactttgggt cagagtcgca aggatttatg acgggaacgg agggatatgt cacatacgga     300
tccccggcgg gtgattttac cgtatattgg gataatcctt acgttggttc ggattcttca     360
agtgcgacat gccctcgggg atacgaaaag gttaaatcgg acagtgcagg gaacaacgca     420
acgctgaaag ttgtgttcta tgaaaatagc taa                                 453
```

<210> SEQ ID NO 37
<211> LENGTH: 354
<212> TYPE: DNA
<213> ORGANISM: Artificial Sequence
<220> FEATURE:
<223> OTHER INFORMATION: Maize optimized SMIP1Aa.

<400> SEQUENCE: 37

```
atggccgcca ggtcctacga gatcgccatc gtgaacctga ccgacgtgga gttcaccagg      60
aaggaggccc acctggacca cggcgtgtgg tccaaggacg gcaactacac cccgccggac     120
aagatctcca ccgccagac cgcccacttc ggctccgagt cccagggcgt ggccaccggc     180
accgagggcc acgtgatcta ctcctcctcc gccggcgact caggtggga ctgggacaac     240 ccgtacatcg gcggcgactc ctcctccgcc aagtgcccgc cgtcctacga gaaggtgctg     300
tccgactcca agggcaacga cgccaccctg aaggtggtgt tctacaagaa gtcc           354
```

<210> SEQ ID NO 38
<211> LENGTH: 354
<212> TYPE: DNA
<213> ORGANISM: Artificial Sequence
<220> FEATURE:
<223> OTHER INFORMATION: Maize optimized SMIP1Aa-W78F/A92L.

<400> SEQUENCE: 38

-continued

```
atggccgcca ggtcctacga gatcgccatc gtgaacctga ccgacgtgga gttcaccagg         60
aaggaggccc acctggacca cggcgtgtgg tccaaggacg gcaactacac cccgccggac        120
aagatctcca ccggccagac cgcccacttc ggctccgagt cccagggcgt ggccaccggc        180
accgagggcc acgtgatcta ctcctcctcc gccggcgact tcagggtgga cttcgacaac        240
ccgtacatcg gcggcgactc ctcctccgcc aagctgccgc cgtcctacga gaaggtgctg        300
tccgactcca agggcaacga cgccaccctg aaggtggtgt tctacaagaa gtcc             354
```

<210> SEQ ID NO 39
<211> LENGTH: 354
<212> TYPE: DNA
<213> ORGANISM: Artificial Sequence
<220> FEATURE:
<223> OTHER INFORMATION: Maize optimized SMIP1Aa-A71L/A90L.

<400> SEQUENCE: 39

```
atggccgcca ggtcctacga gatcgccatc gtgaacctga ccgacgtgga gttcaccagg         60
aaggaggccc acctggacca cggcgtgtgg tccaaggacg gcaactacac cccgccggac        120
aagatctcca ccggccagac cgcccacttc ggctccgagt cccagggcgt ggccaccggc        180
accgagggcc acgtgatcta ctcctcctcc ctgggcgact caggggtgga ctgggacaac        240
ccgtacatcg gcggcgactc ctcctccctg aagtgcccgc cgtcctacga gaaggtgctg        300
tccgactcca agggcaacga cgccaccctg aaggtggtgt tctacaagaa gtcc             354
```

<210> SEQ ID NO 40
<211> LENGTH: 453
<212> TYPE: DNA
<213> ORGANISM: Artificial Sequence
<220> FEATURE:
<223> OTHER INFORMATION: Maize optimized SMIP2Aa.

<400> SEQUENCE: 40

```
atgtccgaga acgtgaccgg cgcccacccg tacggctcca tccactgggt gccggagatc     60
ttcgtggacc cggccaagtc caggggcgag caggacatgg ccgccaggtc ctacgacatc    120
tccatcgtga acctgaccaa catggagctg accagggaga agtcccacct ggaccacggc    180
gtgtggtccg gcgagggctc cgagaccccg ccggacaaga tcgccccggg cgagaccgtg    240
cacttcggct ccgagtccca gggcttcatg accggcaccg agggctacgt gacctacggc    300
tccccggccg gcgacttcac cgtgtactgg gacaacccgt acgtgggctc cgactcctcc    360
tccgccacct gcccgtccgg ctacgagaag gtgaagtccg actccgccgg caacaacgcc    420
accctgaagg tggtgttcta cgagaactcc tga                                 453
```